(12) United States Patent
Lee et al.

(10) Patent No.: US 8,360,321 B2
(45) Date of Patent: Jan. 29, 2013

(54) SYSTEM AND METHOD OF DECONVOLVING MULTIPLEXED FLUORESCENCE SPECTRAL SIGNALS GENERATED BY QUANTUM DOT OPTICAL CODING TECHNOLOGY

(75) Inventors: Jeongjin Lee, Toronto (CA); Warren Che Wor Chan, Toronto (CA); Qing Xiang, Scarborough (CA); Jesse Klostranec, Toronto (CA)

(73) Assignee: FIO Corporation, Toronto (CA)

( * ) Notice: Subject to any disclaimer, the term of this patent is extended or adjusted under 35 U.S.C. 154(b) by 0 days.

(21) Appl. No.: 12/594,430

(22) PCT Filed: Apr. 2, 2008

(86) PCT No.: PCT/CA2008/000623
§ 371 (c)(1),
(2), (4) Date: Jun. 10, 2011

(87) PCT Pub. No.: WO2008/119184
PCT Pub. Date: Oct. 9, 2008

(65) Prior Publication Data
US 2011/0284639 A1 Nov. 24, 2011

(51) Int. Cl.
*G06K 7/10* (2006.01)
(52) U.S. Cl. .............. 235/468; 235/491; 250/459.1
(58) Field of Classification Search ............. 235/459.1, 235/458.1, 468, 491
See application file for complete search history.

(56) References Cited

U.S. PATENT DOCUMENTS

| | | |
|---|---|---|
| 5,244,630 A | 9/1993 | Khalil et al. |
| 5,662,824 A | 9/1997 | Sang et al. |
| 5,714,390 A | 2/1998 | Hallowitz et al. |
| 5,786,219 A | 7/1998 | Zhang et al. |

(Continued)

FOREIGN PATENT DOCUMENTS

| | | |
|---|---|---|
| CA | 2061574 | 8/1992 |
| CA | 2021587 | 4/2003 |

(Continued)

OTHER PUBLICATIONS

Alivisatos, A.P., Perspectives on the Physical Chemistry of Semiconductor Nanocrystals, Journal of Physical Chemistry, 1996, pp. 13226-13239, vol. 100, No. 31, American Chemical Society, USA.

(Continued)

*Primary Examiner* — Daniel Hess
(74) *Attorney, Agent, or Firm* — Jennifer E. Lacroix, Esq.; DLA Piper LLP (US)

(57) ABSTRACT

A method deconvolves a multiplexed fluorescence spectral signal into its component single-color fluorescence spectra emitted by contributing fluorophore types. A spectral database contains a parameter set for each of the component spectra. Optical codes are received as the multiplexed signals. A sliding window technique estimates a number and location of local peaks for the component spectra. Allowable variation ranges are assigned for the corresponding parameter sets. Each multiplexed signal is deconvolved into a sum of parametric values to generate a list of its component spectra. Encoded and received optical codes, in the form of multiplexed signals, are decoded and identified by their component spectra and contributing fluorophore types. A system for deconvolving the multiplexed signals includes a spectral database containing the parameter sets, a detection element receiving the optical codes, and a signal processor encoded to analyze and deconvolve the multiplexed signals.

40 Claims, 8 Drawing Sheets

U.S. PATENT DOCUMENTS

| | | | |
|---|---|---|---|
| 5,817,458 | A | 10/1998 | King et al. |
| 5,837,442 | A | 11/1998 | Tsang |
| 6,011,252 | A | 1/2000 | Jensen |
| 6,022,500 | A | 2/2000 | John et al. |
| 6,066,243 | A | 5/2000 | Anderson et al. |
| 6,100,541 | A | 8/2000 | Nagle et al. |
| 6,103,379 | A | 8/2000 | Margel et al. |
| 6,114,038 | A | 9/2000 | Castro et al. |
| 6,119,953 | A | 9/2000 | Ganan-Calvo et al. |
| 6,172,193 | B1 | 1/2001 | Primi et al. |
| 6,174,469 | B1 | 1/2001 | Ganan-Calvo |
| 6,261,779 | B1 | 7/2001 | Barbera-Guillem et al. |
| 6,274,323 | B1 | 8/2001 | Bruchez et al. |
| 6,309,701 | B1 | 10/2001 | Barbera-Guillem |
| 6,316,781 | B1 | 11/2001 | Nagle et al. |
| 6,319,607 | B1 | 11/2001 | Barbera-Guillem et al. |
| 6,333,110 | B1 | 12/2001 | Barbera-Guillem |
| 6,340,588 | B1 | 1/2002 | Nova et al. |
| 6,353,475 | B1 | 3/2002 | Jensen et al. |
| 6,357,670 | B2 | 3/2002 | Ganan-Calvo |
| 6,399,952 | B1 | 6/2002 | Maher et al. |
| 6,409,900 | B1 | 6/2002 | Parce et al. |
| 6,413,401 | B1 | 7/2002 | Chow et al. |
| 6,430,512 | B1 | 8/2002 | Gallagher |
| 6,468,808 | B1 | 10/2002 | Nie et al. |
| 6,494,830 | B1 | 12/2002 | Wessel |
| 6,498,353 | B2 | 12/2002 | Nagle et al. |
| 6,504,607 | B2 | 1/2003 | Jensen et al. |
| 6,506,609 | B1 | 1/2003 | Wada et al. |
| 6,514,399 | B1 | 2/2003 | Parce et al. |
| 6,524,793 | B1 | 2/2003 | Chandler et al. |
| 6,528,165 | B2 | 3/2003 | Chandler |
| 6,544,732 | B1 | 4/2003 | Chee et al. |
| 6,548,171 | B1 | 4/2003 | Barbera-Guillem et al. |
| 6,548,264 | B1 | 4/2003 | Tan et al. |
| 6,554,202 | B2 | 4/2003 | Ganan-Calvo |
| 6,576,155 | B1 | 6/2003 | Barbera-Guillem |
| 6,592,821 | B1 | 7/2003 | Wada et al. |
| 6,592,822 | B1 | 7/2003 | Chandler |
| 6,630,307 | B2 | 10/2003 | Bruchez et al. |
| 6,632,655 | B1 | 10/2003 | Mehta et al. |
| 6,649,138 | B2 | 11/2003 | Adams et al. |
| 6,673,662 | B2 | 1/2004 | Singh |
| 6,680,211 | B2 | 1/2004 | Barbera-Guillem et al. |
| 6,699,723 | B1 | 3/2004 | Weiss et al. |
| 6,720,411 | B2 | 4/2004 | Mirkin et al. |
| 6,734,420 | B2 | 5/2004 | Empedocles et al. |
| 6,740,491 | B2 | 5/2004 | Mirkin et al. |
| 6,752,966 | B1 | 6/2004 | Chazan |
| 6,759,235 | B2 | 7/2004 | Empedocles et al. |
| 6,767,706 | B2 | 7/2004 | Quake et al. |
| 6,772,070 | B2 | 8/2004 | Gilmanshin et al. |
| 6,773,812 | B2 | 8/2004 | Chandler et al. |
| 6,778,724 | B2 | 8/2004 | Wang et al. |
| 6,787,088 | B2 | 9/2004 | Parce et al. |
| 6,835,326 | B2 | 12/2004 | Barbera-Guillem |
| 6,872,249 | B2 | 3/2005 | Peng et al. |
| 6,881,537 | B1 | 4/2005 | Goudsmit et al. |
| 6,881,821 | B2 | 4/2005 | Simmonds et al. |
| 6,890,764 | B2 | 5/2005 | Chee et al. |
| 6,905,885 | B2 | 6/2005 | Colston et al. |
| 6,966,880 | B2 | 11/2005 | Boecker et al. |
| 6,978,212 | B1 | 12/2005 | Sunshine |
| 6,986,837 | B2 | 1/2006 | Chow et al. |
| 7,037,729 | B2 | 5/2006 | Nie et al. |
| 7,041,362 | B2 | 5/2006 | Barbera-Guillem |
| 7,069,191 | B1 | 6/2006 | Moore |
| 7,077,328 | B2 | 7/2006 | Krichnaswamy et al. |
| 7,079,241 | B2 | 7/2006 | Empedocles et al. |
| 7,166,475 | B2 | 1/2007 | Colyer et al. |
| 7,171,983 | B2 | 2/2007 | Chien et al. |
| 7,192,785 | B2 | 3/2007 | Nie et al. |
| 7,243,670 | B2 | 7/2007 | Witt et al. |
| 7,252,928 | B1 | 8/2007 | Hafeman et al. |
| 7,267,799 | B1 | 9/2007 | Borich et al. |
| 7,729,750 | B2 * | 6/2010 | Tromberg et al. ............ 600/476 |
| 2001/0027918 | A1 | 10/2001 | Parce et al. |
| 2001/0028055 | A1 | 10/2001 | Fafard et al. |
| 2001/0046602 | A1 | 11/2001 | Chandler et al. |
| 2001/0055764 | A1 | 12/2001 | Empedocles et al. |
| 2002/0009728 | A1 | 1/2002 | Bittner et al. |
| 2002/0022273 | A1 | 2/2002 | Empedocles et al. |
| 2002/0031783 | A1 | 3/2002 | Empedocles et al. |
| 2002/0037499 | A1 | 3/2002 | Quake et al. |
| 2002/0045045 | A1 | 4/2002 | Adams et al. |
| 2002/0048425 | A1 | 4/2002 | McBride et al. |
| 2002/0051971 | A1 | 5/2002 | Stuelpnagel et al. |
| 2002/0059030 | A1 | 5/2002 | Otworth et al. |
| 2002/0066401 | A1 | 6/2002 | Peng et al. |
| 2002/0118355 | A1 | 8/2002 | Worthington et al. |
| 2002/0144644 | A1 | 10/2002 | Zehnder et al. |
| 2002/0164271 | A1 | 11/2002 | Ho |
| 2002/0182609 | A1 | 12/2002 | Arcot |
| 2003/0003441 | A1 | 1/2003 | Colston et al. |
| 2003/0017264 | A1 | 1/2003 | Treadway et al. |
| 2003/0026740 | A1 | 2/2003 | Staats |
| 2003/0073086 | A1 | 4/2003 | Guire et al. |
| 2003/0099940 | A1 | 5/2003 | Empedocles et al. |
| 2003/0132538 | A1 | 7/2003 | Chandler |
| 2003/0148530 | A1 | 8/2003 | Lauks |
| 2003/0148544 | A1 | 8/2003 | Nie et al. |
| 2003/0157327 | A1 | 8/2003 | Barbera-Guillem et al. |
| 2003/0165951 | A1 | 9/2003 | Bruchez, Jr. et al. |
| 2003/0170613 | A1 | 9/2003 | Straus et al. |
| 2003/0172043 | A1 | 9/2003 | Guyon et al. |
| 2003/0175773 | A1 | 9/2003 | Chee et al. |
| 2003/0176183 | A1 | 9/2003 | Drucker et al. |
| 2003/0177038 | A1 | 9/2003 | Rao |
| 2003/0177941 | A1 | 9/2003 | Barbera-Guillem |
| 2003/0190628 | A1 | 10/2003 | Nakao et al. |
| 2003/0194350 | A1 | 10/2003 | Stamatelos et al. |
| 2004/0009341 | A1 | 1/2004 | Naasani |
| 2004/0067485 | A1 | 4/2004 | Mayes et al. |
| 2004/0072428 | A1 | 4/2004 | Sato et al. |
| 2004/0096363 | A1 | 5/2004 | Porter |
| 2004/0101621 | A1 | 5/2004 | Adams et al. |
| 2004/0106218 | A1 | 6/2004 | Wang et al. |
| 2004/0118684 | A1 | 6/2004 | Wainright et al. |
| 2004/0147031 | A1 | 7/2004 | Nakao |
| 2004/0176704 | A1 | 9/2004 | Stevens et al. |
| 2004/0203170 | A1 | 10/2004 | Barbera-Guillem |
| 2004/0204633 | A1 | 10/2004 | Rentea et al. |
| 2004/0229261 | A1 | 11/2004 | Young |
| 2004/0241424 | A1 | 12/2004 | Barbera-Guillem |
| 2004/0241752 | A1 | 12/2004 | Anderson et al. |
| 2004/0247861 | A1 | 12/2004 | Naasani |
| 2004/0248163 | A1 * | 12/2004 | Kramer et al. ............ 435/6 |
| 2004/0248167 | A1 | 12/2004 | Quake et al. |
| 2004/0266022 | A1 | 12/2004 | Sundararajan et al. |
| 2004/0267568 | A1 | 12/2004 | Chandler et al. |
| 2005/0004346 | A1 | 1/2005 | Dziegiel et al. |
| 2005/0009002 | A1 | 1/2005 | Chen et al. |
| 2005/0011764 | A1 | 1/2005 | Berndt et al. |
| 2005/0014134 | A1 | 1/2005 | West et al. |
| 2005/0032047 | A1 | 2/2005 | Simmonds et al. |
| 2005/0043894 | A1 | 2/2005 | Fernandez et al. |
| 2005/0059030 | A1 | 3/2005 | Bao et al. |
| 2005/0071199 | A1 | 3/2005 | Riff |
| 2005/0106257 | A1 | 5/2005 | Albayrak |
| 2005/0112277 | A1 | 5/2005 | Banerjee et al. |
| 2005/0120946 | A1 | 6/2005 | Hines et al. |
| 2005/0128479 | A1 | 6/2005 | Gilbert et al. |
| 2005/0164264 | A1 | 7/2005 | Shipwash |
| 2005/0214536 | A1 | 9/2005 | Schrier et al. |
| 2005/0221296 | A1 | 10/2005 | Simmonds et al. |
| 2005/0227370 | A1 | 10/2005 | Ramel et al. |
| 2005/0239118 | A1 | 10/2005 | Goudsmit et al. |
| 2006/0008921 | A1 | 1/2006 | Daniels et al. |
| 2006/0012784 | A1 | 1/2006 | Ulmer |
| 2006/0014040 | A1 | 1/2006 | Peng et al. |
| 2006/0019098 | A1 | 1/2006 | Chan et al. |
| 2006/0029267 | A1 | 2/2006 | Frost et al. |
| 2006/0046330 | A1 | 3/2006 | Chen et al. |
| 2006/0063160 | A1 | 3/2006 | West et al. |
| 2006/0068203 | A1 | 3/2006 | Ying et al. |
| 2006/0078490 | A1 | 4/2006 | Shih et al. |
| 2006/0105335 | A1 | 5/2006 | Daehne et al. |

| | | | |
|---|---|---|---|
| 2006/0152372 | A1 | 7/2006 | Stout |
| 2006/0169800 | A1 | 8/2006 | Rosell |
| 2006/0173715 | A1 | 8/2006 | Wang |
| 2006/0194030 | A1 | 8/2006 | Barbera-Guillem |
| 2007/0020779 | A1 | 1/2007 | Stavis et al. |
| 2007/0031283 | A1 | 2/2007 | Davis et al. |
| 2007/0081920 | A1 | 4/2007 | Murphy et al. |
| 2008/0272312 | A1* | 11/2008 | Tuschel ............ 250/459.1 |

FOREIGN PATENT DOCUMENTS

| | | |
|---|---|---|
| CA | 2518352 | 3/2005 |
| EP | 1315099 | 5/2003 |
| JP | 2002-271 | 1/2002 |
| JP | 2005-508493 | 3/2005 |
| WO | 99/19000 | 4/1999 |
| WO | 99/36564 | 7/1999 |
| WO | 99/64840 | 12/1999 |
| WO | 99/66318 | 12/1999 |
| WO | 00/13580 | 3/2000 |
| WO | 00/28598 | 5/2000 |
| WO | 00/70080 | 11/2000 |
| WO | 01/20533 | 3/2001 |
| WO | 01/89585 | 11/2001 |
| WO | 01/93754 | 12/2001 |
| WO | 02/04484 | 1/2002 |
| WO | 03/003015 | 1/2003 |
| WO | 2004/008550 | 1/2004 |
| WO | 2004/040319 | 5/2004 |
| WO | 2005/023923 | 3/2005 |
| WO | 2005/031802 | 4/2005 |
| WO | 2005/052996 | 6/2005 |
| WO | 2005/053649 | 6/2005 |
| WO | 2005/061095 | 7/2005 |
| WO | 2006/033732 | 3/2006 |
| WO | 2006/045004 | 4/2006 |
| WO | 2006/072306 | 7/2006 |
| WO | 2006/132953 | 12/2006 |
| WO | 2007/011622 | 1/2007 |
| WO | 2008/089155 | 7/2008 |
| WO | 2008/147382 | 12/2008 |
| WO | 2009/059404 | 5/2009 |

OTHER PUBLICATIONS

Bakalova, Rurniana et al., Quantum dot-conjugated hybridization probes for preliminary screening of siRNA sequences, Journal of the American Chemical Society, Aug. 1, 2005, pp. 11328-11335, vol. 127, No. 32, American Chemical Society, USA.

Boldt, Klaus et al., Comparative Examination of the Stability of Semiconductor Quantum Dots in Various Biochemical Buffers, Journal of Physical Chemistry B, 2006, pp. 1959-1963, vol. 110, No. 5, American Chemical Society, USA.

Branch, Mary Ann et al., A Subspace, Interior, and Conjugate Gradient Method for Large-Scale Bound-Constrained Minimization Problems, SIAM J. Sci. Comput., Aug. 3, 1999, pp. 1-23, vol. 21, No. 1, Society for Industrial and Applied Mathematics.

Bruchez, Marcel Jr. et al., Semiconductor Nanocrystals as Fluorescent Biological Labels, Science, Sep. 25, 1998, pp. 2013-2015, vol. 281, American Association for the Advancement of Science, USA.

Burns, Mark A. et al., An Integrated Nanoliter DNA Analysis Device, Science, Oct. 16, 1998, pp. 484-487, vol. 282, No. 5388, American Association for the Advancement of Science, USA.

Chabinyc, Michael L. et al., An Integrated Fluorescence Detection System in Poly(dimethylsiloxane) for Microfluidic Applications, Analytical Chemistry, Sep. 15, 2001, pp. 4494-4498, vol. 73, No. 18, American Chemical Society, USA.

Chan, Eugene Y. et al., DNA Mapping Using Microfluidic Stretching and Single-Molecule Detection of Fluorescent Site-Specific Tags, Genome Research, 2004, pp. 1137-1146, vol. 14, Cold Spring Harbour Laboratory Press, USA.

Chan, Warren C.W. et al., Luminescent quantum dots for multiplexed biological detection and imaging, Current Opinion in Biotechnology, 2002, pp. 40-46, vol. 13, Elsevier Science Ltd.

Chan, Warren C.W. et al., Quantum Dot Bioconjugates for Ultrasensitive Nonisotopic Detection, Science, Sep. 25, 1998, pp. 2016-2018, vol. 281, American Association for the Advancement of Science, USA.

Chou, Hou-Pu et al., A microfabricated device for sizing and sorting DNA molecules, PNAS—Proceedings of the National Academy of Sciences of the United States of America, Jan. 1999, pp. 11-13, vol. 96, The National Academy of Sciences, USA.

Dabbousi, B.O. et al., (CdSe)ZnS Core-Shell Quantum Dots: Synthesis and Characterization of a Size Series of Highly Luminescent Nanocrystallites, Journal of Physical Chemistry B, 1997, pp. 9463-9475, vol. 101, No. 46, American Chemical Society, USA.

Duffy, D.C. et al., Rapid Prototyping Of Microfulidic Systems in Poly(dimethylsiloxane), Analytical Chemistry, Dec. 1, 1998, pp. 4974-4984, vol. 70, No. 23, American Chemical Society, USA.

Eisenstein, Michael, Technology Feature: Protein Arrays—Growing pains, Losing the Label, an Apt Solution? & (Almost) No Assembly Required, Nature, Dec. 14, 2006, pp. 959-962, vol. 444, Nature Publishing Group, USA.

Fournier-Bidoz, Sebastien et al., Facile and Rapid One-Step Mass Preparation of Quantum-Dot Barcodes, Angewandte Chemie International Edition, 2008, pp. 5577-5581, vol. 47, No. 30, Wiley-VCH Verlag GmbH & Co. KGaA, Weinheim.

Fu, Anne Y. et al., A microfabricated fluorescence-activated cell sorter, Nature Biotechnology, Nov. 1999, pp. 1109-1111, vol. 17, Nature America Inc., USA.

Fu, Lung-Ming et al., Multiple injection techniques for microfluidic sample handling, Electrophoresis, 2003, pp. 3026-3032, vol. 24, Wiley-VCH Verlag GmbH & Co. KGaA, Weinheim.

Gao, Xiaohu et al., In vivo cancer targeting and imaging with semiconductor quantum dots, Nature Biotechnology, Jul. 18, 2004, pp. 969-976, vol. 22, No. 8, Nature Publishing Group, USA.

Gao, Xiaohu et al., Quantum Dot-Encoded Mesoporous Beads with High Brightness and Uniformity: Rapid Readout Using Flow Cytometry, Analytical Chemistry, Apr. 15, 2004, pp. 2406-2410, vol. 76, No. 8, American Chemical Society, USA.

Gao, Xiaohu et al., Quantum-dot nanocrystals for ultrasensitive biological labelling and mulitcolor optical encoding, Journal of Biomedical Optics, Oct. 2002, pp. 532-537, vol. 7, No. 4, SPIE.

Gaponik, Nikolai et al., Toward Encoding Combinatorial Libraries: Charge-Driven Microencapsulation of Semiconductor Nanocrystals Luminescing in the Visible and Near IR, Advanced Materials, Jun. 18, 2002, pp. 879-882, vol. 14, No. 12, Wiley-VCH Verlag GmbH, Weinheim.

Gershon, Diane, Technology Feature: DNA Microarrays—More than than gene expression, It's a Small World, Microassays Move Downstream & On the Hardware Front, Nature, Oct. 20, 2005, pp. 1195-1198, vol. 437, Nature Publishing Group, USA.

Goluch, E.D. et al., A bio-barcode assay for on-chip attomolar-sensitivity protein detection, Lab on a Chip, Aug. 15, 2006, pp. 1293-1299, vol. 6, The Royal Society of Chemistry.

Grumann, M. et al., Parallelization of Chip-Based Fluorescence Immuno-Assays with Quantum-Dot Labelled Beads, The 13th International Conference on Solid-State Sensors, Actuators and Microsystems, Jun. 2005, pp. 1114-1117, IEEE.

Han, Mingyong et al., Quantum-dot-tagged microbeads for multiplexed optical coding of biomolecules, Nature Biotechnology, Jul. 2001, pp. 631-635, vol. 19, Nature Publishing Group, USA.

Hines, Margaret A. et al., Synthesis and Characterization of Strongly Luminescing ZnS-Capped CdSe Nanocrystals, Journal of Physical Chemistry B, 1996, pp. 468-471, vol. 100, No. 2, American Chemical Society, USA.

Kloepfer, Jeremiah A. et al., Photophysical Properties of Biologically Compatible CdSe Quantum Dot Structures, Journal of Physical Chemistry B, 2005, pp. 9996-10003, vol. 109, No. 20, American Chemical Society, USA.

Klostranec, Jesse M. et al., Convergence of Quantum Dot Barcodes with Microfluidics and Signal Processing for Multiplexed High-Throughput Infectious Disease Diagnostics, Nano Letters, Aug. 18, 2007, pp. 2812-2818, vol. 7, No. 9, American Chemical Society, USA.

Klostranec, Jesse M. et al., Quantum Dots in Biological and Biomedical Research: Recent Progress and Present Challenges, Advanced Materials, Aug. 4, 2006, pp. 1953-1964, vol. 18, No. 15, Wiley-VCH Verlag GmbH & Co. KGaA, Weinheim.

Li, Yougen et al., Multiplexed detection of pathogen DNA with DNA-based fluorescence nanobarcodes, Nature Biotechnology, Jul. 2005, pp. 885-889, vol. 23, No. 7, Nature Publishing Group, USA.

Liu, Wen-Tso et al., Microfluidic device as a new platform for immunofluorescent detection of viruses, Lab on a Chip, Oct. 4, 2005, pp. 1327-1330, vol. 5, The Royal Society of Chemistry.

Malamud, D. et al., Point Detection of Pathogens in Oral Samples, Adv Dent Res, Jun. 2005, pp. 12-16, vol. 18.

Marti et al., Design and characterization of two-dye and three-dye binary fluorescent probes for mRNA detection, Tetrahedron, Mar. 21, 2007, pp. 3591-3600, vol. 63, No. 17, Elsevier Science Publishers, Amsterdam, NL.

Mattoussi, H. et al., Luminescent Quantum Dot-Bioconjugates in Immunoassays, FRET, Biosensing, and Imaging Applications, JALA—Journal of the Association for Laboratory Automation, Feb. 2004, pp. 28-32, vol. 9, No. 1, The Association for Laboratory Automation, USA.

Medintz, Igor L. et al., Quantum dot bioconjugates for imaging, labelling and sensing, Nature Materials, Jun. 2005, pp. 435-446, vol. 4, Nature Publishing Group, USA.

Moré, Jorge J. et al., Computing a Trust Region Step, SIAM J. Sci. Stat. Comput., Sep. 1983, pp. 553-572, vol. 4, No. 3, Society for Industrial and Applied Mathematics.

Murray, C.B. et al., Synthesis and Characterization of Nearly Monodisperse CdE (E=S, Se, Te) Semiconductor Nanocrystallites, Journal of the American Chemical Society, 1993, pp. 8706-8715, vol. 115, No. 19, American Chemical Society, USA.

Neogi, A. et al., Enhanced luminescence efficiency from hydrogel microbead encapsulated quantum dots, Materials Research Society Symposium Proceedings, Jan. 1, 2007, pp. 202-207, vol. 959, Materials Research Society, USA.

Peng, Xiaogang et al., Epitaxial Growth of Highly Luminescent CdSe/CdS Core/Shell Nanocrystals with Photostability and Electronic Accessibility, Journal of the American Chemical Society, 1997, pp. 7019-7029, vol. 119, No. 30, American Chemical Society, USA.

Pregibon, Daniel C. et al., Multifunctional Encoded Particles for High-Throughput Biomolecule Analysis, Science, Mar. 9, 2007, pp. 1393-1396, vol. 315, American Association for the Advancement of Science, USA [downloaded on Mar. 9, 2009 from http://www.science mag.org].

Sathe, Tushar R. et al., Mesoporous Silica Beads Embedded With Semiconductor Quantum Dots and Iron Oxide Nanocrystals: Dual-Function Microcarriers for Optical Encoding and Magnetic Separation, Analytical Chemistry, Jul. 20, 2006, pp. 5627-5632, vol. 78, No. 16, American Chemical Society, USA.

Service, Robert F., DNA Analysis: Microchip Arrays Put DNA On The Spot, Science, Oct. 16, 1998, pp. 396-399, vol. 282, No. 5388, American Association for the Advancement of Science, USA [downloaded on Mar. 20, 2008 from http://www.science mag.org/cgi/content/full/282/5388/396].

Stavis, Samuel M. et al., Single molecule studies of quantum dot conjugates in a submicrometer fuidic channel, Lab on a Chip, Jan. 13, 2005, pp. 337-343, vol. 5, The Royal Society of Chemistry.

Sukhanova, A. et al., Nanocrystal-encoded fluorescent microbeads for proteomics: Antibody profiling and diagnostics of autoimmune diseases, Nano Letters, Aug. 2007, pp. 2322-2327, vol. 7, No. 8, American Chemical Society, USA.

Thompson, B. et al, Dispersion Copolymerization of Styrene and Divinylbenzee. II. Effect of Crosslinker on Particle Morphology, Journal of Applied Polymer Science, 1996, pp. 2009-2028, vol. 59, John Wiley & Sons, Inc.

Xu, Hongxia et al., Muliplexed SNP genotyping using the Qbead™ system: a quantum dot-encoded microsphere-based assay, Nucleic Acids Research, 2003, pp. 1-10, vol. 31, No. 8, Oxford University Press.

Xuan, Xiangchun et al., Focused electrophoretic motion and selected electrokinetic dispensing of particles of particles and cells in cross-microchannels, Electrophoresis, 2005, pp. 3552-3560, vol. 26, WILEY-VCH Verlag GmbH & co. KGaA, Weinheim.

Yun, Kwang-Seok et al., A microfluidic chip for measurement of biomolecules using a microbead-based quantum dot fluorescence assay, Measurement Science and Technology, 2006, pp. 3178-3183, vol. 17, IOP Publishing Ltd, UK.

Zaytseva, Natalya V. et al., Development of a microfluidic biosensor module for pathogen detection, Lab on a Chip, Jul. 6, 2005, pp. 805-811, vol. 5, The Royal Society of Chemistry.

* cited by examiner

SYSTEM AND METHOD OF DECONVOLVING MULTIPLEXED FLUORESCENCE SPECTRAL SIGNALS GENERATED BY QUANTUM DOT OPTICAL CODING TECHNOLOGY

FIELD OF THE INVENTION

The present invention relates generally to the field of signal deconvolution, and more particularly, to a system and method of deconvolving mixed fluorescence spectral signals generated by quantum dot (or "QD") optical coding technology.

BACKGROUND OF THE INVENTION

In 2001, academic research labs may have been the first to introduce QD optical coding technology for contemplated uses in biological applications [see, for example, M. Han, X. Gao, J. Z. Su, S. Nie, *Nat. Biotech.*, 2001, 19, 631]. Thus far, however, commercial applications based on the previous work of such academic research labs may have been somewhat slow to develop.

Earlier excitement over the potential biological applications for such QD optical coding (or QD "barcoding") technology may have stemmed, to some degree, from the prospect of making highly sensitive measurements of multiple protein and/or nucleic acid targets on a substantially simultaneous basis. [See, for example: H. Xu, M. Sha, E. Y. Wong, J. Uphoff, Y. Xu, J. A. Treadway, A. Truong, E. O'Brien, S. Asquith, M. Stubbins, N. K. Spurr, E. H. Lai, W. Mahoney, *Nucleic Acids Research*, 2003, 31, e43; and Y. Ho, M. C. Kung, S. Yang, T. Wang, *Nano Lett.*, 2005, 5, 1693.] It may also have been believed that, in comparison to optical signals emitted by organic fluorophores, the use of QDs might enable the generation and use of a greater number of optical codes due to their substantially tunable emission and/or relatively narrow spectral linewidth. [See, for example: M. Bruchez, M. Moronne, P. Gin, S. Weiss, A_P. Alivisatos, *Science*, 1998, 281, 2013; W. C. W. Chan, S. Nie, *Science*, 1998, 281, 2016; A. P. Alivisatos, *J. Phys. Chem.*, 1996, 100, 13226; I. L. Medintz, H. T. Uyeda, E. R. Goldman, H. Mattoussi, *Nat. Mater.*, 2005, 4, 435; and J. M. Klostranec, W. C. W. Chan, *Adv. Mat.*, 2006, 18, 1953.] QD optical codes may additionally have been thought to require only a low-power single excitation source, due to their large absorption cross-section and continuous absorption profile—a factor which might have led to significant reductions in the complexity and cost of instrumentation. Indeed, it may have been suggested that such a system could rival microarray technologies, which are commonly used for measuring large numbers of biological molecules in a short period of time. [See, for example: R. F. Service, *Science*, 1998, 282, 396; D. Gershon, *Nature*, 2005, 437, 1195; and M. Eisenstein, *Nature*, 2006, 444, 959.]

Much effort in recent years may have been focused on the reproducible synthesis of QD optical codes. [See, for example: X. Gao, S. Nie, *Anal. Chem.*, 2004, 76, 2406; T. R. Sathe, A. Agrawal, S. Nie, *Anal. Chem.*, 2006, 78, 5627; and N. Gaponik, I. L. Radtchenko, G. B. Sukhorukov, H. Weller, A. L. Rogach, *Adv. Mat.*, 2002, 14, 879.]

Previously, however, the method of reading QD optical codes and the potential impact of environmental conditions on fluorescence stability of the optical codes may have been largely ignored. Though not essential to the working of the present invention, it may now be believed that, without considering these two constraints, the accurate identification of QD optical codes might be compromised, potentially leading to false assay outcomes. There may, therefore, be a need for a rapid, reliable and accurate method of deconvolving fluorescence spectra generated by QD optical coding technology, in which there is often a large degree of spectral overlap. In addition to signal deconvolution, there is also a need for a method of identifying the QD optical codes that takes into account the impact of environmental factors on fluorescence stability.

It is an object of one preferred embodiment according to the invention to provide a system and/or method for creating, and/or selecting a set of, optical codes (preferably, but not necessarily, QD optical codes) with unique spectral signatures.

It is an object of one preferred embodiment according to the invention to provide a system and/or method for Gaussian curve modeling of single-color fluorophores (preferably, but not necessarily, QDs), preferably but not necessarily for reference use in deconvolving one or more QD optical codes.

It is an object of one preferred embodiment according to the invention to provide for the relatively rapid and/or substantially accurate read-out of QD optical codes.

It is an object of one preferred embodiment according to the invention to provide a system and/or method for making substantially accurate estimates of local peak information for QD optical codes.

It is an object of one preferred embodiment according to the invention to minimize or reduce the chances of falsely identifying QD optical codes.

It is an object of one preferred embodiment according to the invention to provide a system and/or method adapted to deconvolute mixed fluorescence spectral signals in optical codes and/or in mixtures of fluorophores (preferably, but not necessarily, mixtures of QDs).

It is an object of one preferred embodiment according to the invention to provide a system and/or method adapted to deconvolute mixed fluorescence spectral signals composed of one or more, and preferably at least two, unique QD emissions in solution.

It is an object of one preferred embodiment according to the invention to provide a system and/or method that, after deconvolution of a mixed fluorescence spectral signal, generates deconvolved spectra with similar appearance and/or emission wavelengths to single-color QD spectra.

It is an object of one preferred embodiment according to the invention to provide a system and/or method that accurately deconvolves mixed fluorescence spectral signals that possess a large degree of overlap in their component single-color fluorescence spectra.

It is an object of one preferred embodiment according to the invention to provide a system and/or method that may be generalized for use with QD optical codes composed of more than two colors.

It is an object of one preferred embodiment according to the invention to provide a system and/or method for signal deconvolution that accounts, to some degree, for instrumental measurement errors and/or for a specific decoding scheme utilized.

It is an object of one preferred embodiment according to the invention to provide a system and/or method for screening out ambiguous QD combinations from a set of selected QD optical codes.

It is an object of one preferred embodiment according to the invention to provide a set of QD optical codes that is advantageously selected to balance accurate read-out with a high number of usable barcodes.

It is an object of one preferred embodiment according to the invention to provide a system and/or method that minimizes or reduces risks associated with measurement error.

It is an object of one preferred embodiment according to the invention to provide a system and/or method that is adapted for use in situations where microbead size and/or doping yields cannot be precisely controlled.

It is an object of one preferred embodiment according to the invention to provide a system and/or method that enables selection of a relatively reliable detection scheme based on known sources and/or patterns of signal variation amongst QD optical codes.

It is an object of one preferred embodiment according to the invention to provide a system and/or method that is adaptable for use in different environmental conditions, such as, for example, in varying storage buffer types and pHs.

It is an object of one preferred embodiment according to the invention to provide a system and/or method that is adaptable to be used with QDs of various sizes.

It is an object of one preferred embodiment according to the invention to provide a system and/or method for use in biological and/or medical applications.

It is an object of the present invention to obviate or mitigate one or more of the aforementioned mentioned disadvantages associated with the prior art, and/or to achieve one or more of the aforementioned objects of the invention.

SUMMARY OF THE INVENTION

According to the invention, there is disclosed a method of deconvolving a mixed (or multiplexed) fluorescence spectral signal received from multiple QD types in a QD optical code. The method de-mixes the multiplexed fluorescence spectral signal into multiple single-color fluorescence spectra—i.e., a single-color fluorescence spectrum for each of the QD types contributing to the mixed fluorescence spectral signal—thereby differentiating the fluorescence spectra received from each of the QD types in a mixture (or in a QD optical code).

The method may preferably also include a further QD optical code set selection step, and/or a QD optical code differentiation step, wherein a set of QD optical codes is selected so as to facilitate the differentiation of multiple QD optical codes, and/or wherein the members of a pre-selected set of QD optical codes are differentiated from one another. According to the invention, and given a potential measurement error, the discrimination of different QD optical codes based on combinations of the same QD types may be facilitated by initially selecting a set of QD optical codes so as to reduce, minimize, and/or eliminate overlap of—and/or the members of a pre-selected set of QD optical codes may be differentiated from one another based on—(a) measured absolute fluorescence intensities for the QD types in different QD optical codes; and/or (b) QD type fluorescence intensity ratios for different QD optical codes. This latter method of selecting a set of QD optical codes, and differentiating between members of the set, may alternately hereinafter be referred to as a "ratiometric" method or technique.

According to an aspect of one preferred embodiment of the invention, the system and method of deconvolving mixed fluorescence spectral signals which may be generated by QD optical coding technology preferably includes the ratiometric method for selecting a set of QD optical codes and/or for differentiating the members of a pre-selected set of QD optical codes from one another.

According to the invention, there is also disclosed a system for implementing the above-described methods.

Now, with a slight shift in focus, it is also noted that, according to the invention, there is disclosed a method of deconvolving a mixed fluorescence spectral signal into its component single-color fluorescence spectra emitted by contributing fluorophore types. The method includes a database providing step, a receiving step, and an analysis step of analyzing each mixed fluorescence spectral signal. In the database providing step, a spectral database is provided that contains parameter sets, one for each of the component single-color fluorescence spectra. In the receiving step, one or more encoded optical codes are received, each in the form of one aforesaid mixed fluorescence spectral signal emitted by a combination of the contributing fluorophore types. The analysis step includes a peak estimation substep, a constraint setup substep, and a deconvolution substep. In the peak estimation substep, a sliding window technique is used, with reference to the parameter sets contained in the spectral database, to initially identify and estimate the number and location of local peak regions for each of the component single-color fluorescence spectra. In the constraint setup substep, allowable variation ranges are assigned for each of the parameter sets corresponding to one of the local peak regions for each the component single-color fluorescence spectra. In the deconvolution substep, the mixed fluorescence spectral signal is deconvolved into a sum of parametric values, with reference to the parameter sets contained in the spectral database, so as to generate a list of its component single-color fluorescence spectra. In this manner, each encoded and received one of the optical codes, in the form of one aforesaid mixed fluorescence spectral signal, is decoded and identified by its component single-color fluorescence spectra corresponding to its contributing fluorophore types.

According to an aspect of one preferred embodiment of the invention, one or more of the contributing fluorophore types are contributing quantum dot (QD) types, and one or more of the encoded optical codes are encoded QD optical codes.

According to an aspect of one preferred embodiment of the invention, in the constraint setup substep, one or more weighting factors may preferably, but need not necessarily, be assigned for each of the local peak regions.

According to an aspect of one preferred embodiment of the invention, the method may preferably, but need not necessarily, also include a curve modelling step before the database providing step. In the curve modeling step, (i) an automated non-linear optimization technique may preferably, but need not necessarily, be used to reduce each of the component single-color fluorescence spectra to a Gaussian curve, and (ii) the parameter sets for each of the component single-color fluorescence spectra may preferably, but need not necessarily, be generated and recorded in the spectral database. In the deconvolution substep, the parametric values may preferably, but need not necessarily, be Gaussian parametric values.

According to an aspect of one preferred embodiment of the invention, the automated non-linear optimization technique may preferably, but need not necessarily, be a trust-region (TR) fitting technique.

According to an aspect of one preferred embodiment of the invention, in the curve modelling step, the automated non-linear optimization technique may preferably, but need not necessarily, minimize the first two terms of a Taylor approximation to an error function.

According to an aspect of one preferred embodiment of the invention, the error function may preferably, but need not necessarily, be the difference between data and the objective curve function.

According to an aspect of one preferred embodiment of the invention, in the curve modelling step, the automated non-linear optimization technique may preferably, but need not necessarily, be performed according to the formula $$a_k \exp\left\{-\left(\frac{x-b_k}{c_k}\right)^2\right\}$$
$$k = 1, \ldots, N,$$

where a, b, and c are three parametric curve values representing each of the component single-color fluorescence spectra, and where N is a number of fluorophore types from which the contributing fluorophore types present in the mixed fluorescence spectral signal are selected. In the database providing step, each of the parameter sets contained in the spectral database may preferably, but need not necessarily, be provided in the form {a, b, and c}. In the deconvolution substep, the mixed fluorescence spectral signal may preferably, but need not necessarily, be deconvolved according to the formula $$\sum_{m=1}^{M} A_m \exp\left\{-\left(\frac{x-B_m}{C_m}\right)^2\right\},$$

where M is the number of component single-color fluorescence spectra in the mixed fluorescence spectral signal. The list of the component single-color fluorescence spectra in the mixed fluorescence spectral signal may preferably, but need not necessarily, be provided in the form $\{A_k, B_k, C_k\}$ where $k=1, \ldots, M$.

According to an aspect of one preferred embodiment of the invention, the contributing fluorophore types in each aforesaid combination may preferably, but need not necessarily, have measurable absolute fluorescence intensities. The method may also preferably include a set selection step before the receiving step. In the set selection step, an optimal set of the optical codes may preferably, but need not necessarily, be selected. Each of the optical codes may preferably, but need not necessarily, be selected such that, given a predetermined maximum potential measurement error, measured absolute fluorescence intensities for each aforesaid combination of the contributing fluorophore types are discrete from one another.

According to an aspect of one preferred embodiment of the invention, the method may preferably, but need not necessarily, also include a differentiation step after the deconvolution substep. In the differentiation step, the optical codes may preferably, but need not necessarily, be differentiated from one another on the basis of measured absolute fluorescence intensities of the fluorophore types in each aforesaid combination, given a predetermined maximum potential measurement error.

According to an aspect of one preferred embodiment of the invention, the predetermined maximum potential measurement error may preferably, but need not necessarily, be about ten (10) percent.

According to an aspect of one preferred embodiment of the invention, the fluorophore types in each aforesaid combination may preferably, but need not necessarily, have calculable fluorescence intensity ratios. The method may preferably, but need not necessarily, also include a set selection step before the receiving step. In the set selection step, an optimal set of the optical codes may preferably, but need not necessarily, be selected. Each of the optical codes may preferably, but need not necessarily, be selected such that the fluorescence intensity ratios for each the combination are separated from each other by a predetermined minimum intensity ratio difference (MIRD).

According to an aspect of one preferred embodiment of the invention, the method may preferably, but need not necessarily, also include a differentiation step after the deconvolution substep. In the differentiation step, fluorescence intensity ratios of the fluorophore types in each the combination may preferably, but need not necessarily, be calculated. The optical codes may preferably, but need not necessarily, be differentiated from one another by the calculated fluorescence intensity ratios, given a predetermined minimum intensity ratio difference (MIRD) separating the fluorescence intensity ratios of the fluorophore types for each the combination.

According to an aspect of one preferred embodiment of the invention, the predetermined MIRD may preferably, but need not necessarily, be about 0.3.

According to an aspect of one preferred embodiment of the invention, for each of the optical codes, the combination of its contributing fluorophore types may preferably, but need not necessarily, be contained within a microbead that is adapted for detection of a target molecule within a clinical sample.

According to an aspect of one preferred embodiment of the invention, the method may preferably, but need not necessarily, also include an irradiation step before the receiving step. In the irradiation step, the combination of the contributing fluorophore types may preferably, but need not necessarily, be irradiated with electromagnetic frequency (EMF) radiation. As such, the combination may preferably, but need not necessarily, emit the mixed fluorescence spectral signal.

According to an aspect of one preferred embodiment of the invention, in the irradiation step, a laser may preferably, but need not necessarily, irradiate the combination.

According to an aspect of one preferred embodiment of the invention, the EMF radiation may preferably, but need not necessarily, have an EMF wavelength of about 488 nm.

According to an aspect of one preferred embodiment of the invention, the database providing step, the receiving step, and the analysis step may preferably, but need not necessarily, be performed onboard a handheld detection device.

According to an aspect of one preferred embodiment of the invention, the contributing fluorophore types may preferably, but need not necessarily, vary from one another based on the color and/or the intensity thereof.

According to an aspect of one preferred embodiment of the invention, each aforesaid combination may preferably, but need not necessarily, vary from each other aforesaid combination based on the color and/or the intensity of its contributing fluorophore types.

According to an aspect of one preferred embodiment of the invention, four colors of contributing fluorophore types may preferably, but need not necessarily, be provided. Five intensities for each of the colors of contributing fluorophore types may preferably, but need not necessarily, be provided.

According to the invention, there is also disclosed a system for deconvolving a mixed fluorescence spectral signal into its component single-color fluorescence spectra emitted by contributing fluorophore types. The system is for use with one or more encoded optical codes. Each of the optical codes is in the form of one aforesaid mixed fluorescence spectral signal emitted by a combination of the contributing fluorophore types. The system includes a spectral database, a detection element, and a signal processor. The spectral database contains parameter sets, one for each of the component single-color fluorescence spectra. The detection element operatively receives the optical codes. The signal processor is operative to analyze each aforesaid mixed fluorescence spectral signal. The signal processor is encoded: (i) to operatively execute a sliding window technique, with reference to the parameter sets contained in the spectral database, for initial identification and estimation of the number and location of local peak regions for each of the component single-color fluorescence spectra; (ii) to assign allowable variation ranges for each of the parameter sets corresponding to one of the local peak regions for each the component single-color fluorescence spectra; and (iii) to operatively deconvolve the mixed fluorescence spectral signal into a sum of parametric values, with reference to the parameter sets contained in the spectral database, so as to generate a list of its the component single-color fluorescence spectra. In this manner, the system decodes and identifies each encoded and received one of the optical codes, in the form of one aforesaid mixed fluorescence spectral signal, by its component single-color fluorescence spectra corresponding to its contributing fluorophore types.

According to an aspect of one preferred embodiment of the invention, the system is adapted for use with contributing quantum dot (QD) types as one of more of the contributing fluorophore types, and encoded QD optical codes as one or more of the encoded optical codes.

According to an aspect of one preferred embodiment of the invention, the signal processor may preferably, but need not necessarily, be additionally encoded to assign one or more weighting factors for each of the local peak regions.

According to an aspect of one preferred embodiment of the invention, the system may preferably, but need not necessarily, also include a fluorometer to measure the component single-color fluorescence spectra for each of the contributing fluorophore types. The system may preferably, but need not necessarily, also include a spectral processor encoded to operatively reduce each of the component single-color fluorescence spectra to a Gaussian curve. The parametric values may preferably, but need not necessarily, be Gaussian parametric values.

According to an aspect of one preferred embodiment of the invention, the spectral processor may preferably, but need not necessarily, reduce each of the component single-color fluorescence spectra to the aforesaid Gaussian curve according to the formula $$a_k \exp\left\{-\left(\frac{x-b_k}{c_k}\right)^2\right\}$$
$$k = 1, \ldots, N,$$

where a, b, and c are three parametric curve values representing each of the component single-color fluorescence spectra, and where N is a number of fluorophore types from which the contributing fluorophore types present in the mixed fluorescence spectral signal are selected. Each of the parameter sets contained in the spectral database may preferably, but need not necessarily, be provided in the form {a, b, and c}. The signal processor may preferably, but need not necessarily, deconvolve the mixed fluorescence spectral signal according to the formula $$\sum_{m=1}^{M} A_m \exp\left\{-\left(\frac{x-B_m}{C_m}\right)^2\right\},$$

where M is the number of component single-color fluorescence spectra in the mixed fluorescence spectral signal. The list of the component single-color fluorescence spectra in the mixed fluorescence spectral signal may preferably, but need not necessarily, be provided in the form $\{A_k, B_k, C_k\}$ where $k=1, \ldots M$.

According to an aspect of one preferred embodiment of the invention, the detection element may preferably, but need not necessarily, be operative to measure absolute fluorescence intensities of contributing fluorophore types in each aforesaid combination. The system may preferably, but need not necessarily, also include a predetermined set of the optical codes. Each of the optical codes in the predetermined set may preferably, but need not necessarily, be such that, given a predetermined maximum potential measurement error, the absolute fluorescence intensities measured for each aforesaid combination of the contributing fluorophore types are discrete from one another.

According to an aspect of one preferred embodiment of the invention, the signal processor may preferably, but need not necessarily, be additionally encoded to operatively differentiate the optical codes from one another on the basis of measured absolute fluorescence intensities of the fluorophore types in each aforesaid combination, given a predetermined maximum potential measurement error.

According to an aspect of one preferred embodiment of the invention, the signal processor may preferably, but need not necessarily, be operative to calculate fluorescence intensity ratios of the fluorophore types in each aforesaid combination. The system may preferably, but need not necessarily, also include a predetermined set of the optical codes. Each of the optical codes in the predetermined set may preferably, but need not necessarily, be such that the fluorescence intensity ratios for each the combination are separated from each other by a predetermined minimum intensity ratio difference (MIRD).

According to an aspect of one preferred embodiment of the invention, the signal processor may preferably, but need not necessarily, be additionally encoded (i) to operatively calculate fluorescence intensity ratios of the fluorophore types in each aforesaid combination, and (ii) to differentiate the optical codes from one another by the calculated fluorescence intensity ratios, given a predetermined minimum intensity ratio difference (MIRD) separating the fluorescence intensity ratios of the fluorophore types for each aforesaid combination.

According to an aspect of one preferred embodiment of the invention, the system may preferably, but need not necessarily, also include a microbead containing the combination of the contributing fluorophore types for each of the optical codes. Each microbead may preferably, but need not necessarily, be adapted for detection of a target molecule within a clinical sample.

According to an aspect of one preferred embodiment of the invention, the system may preferably, but need not necessarily, also include an irradiating element to operatively irradiate the combination of the contributing fluorophore types with electromagnetic frequency (EMF) radiation. As such, the combination may preferably, but need not necessarily, emit the mixed fluorescence spectral signal.

According to an aspect of one preferred embodiment of the invention, the irradiating element may preferably, but need not necessarily, be a laser.

According to an aspect of one preferred embodiment of the invention, the system may preferably, but need not necessarily, also include a handheld detection device enclosure substantially enclosing the detection element and the signal processor. The spectral database may preferably, but need not necessarily, be carried onboard the handheld detection device.

Other advantages, features and characteristics of the present invention, as well as methods of operation and functions of the related elements of the method and system, and the combination of steps, parts and economies of manufacture, will become more apparent upon consideration of the following detailed description and the appended claims with reference to the accompanying drawings, the latter of which are briefly described hereinbelow.

BRIEF DESCRIPTION OF THE DRAWINGS

The novel features which are believed to be characteristic of the system and method according to the present invention, as to their structure, organization, use, and method of operation, together with further objectives and advantages thereof, will be better understood from the following drawings in which presently preferred embodiments of the invention will now be illustrated by way of example. It is expressly understood, however, that the drawings are for the purpose of illustration and description only, and are not intended as a definition of the limits of the invention. In the accompanying drawings:

FIG. 3a is a graphical representation of individual spectra for two single-color QD types before multiplexing;

FIG. 3b is a graphical representation of a mixed (or multiplexed) fluorescence spectral signal emitted by the QD types represented in FIG. 3a;

FIG. 3c is a graphical representation of deconvolved single-color fluorescence spectra, one for each of the QD types contributing to the mixed fluorescence spectral signal of FIG. 3b;

FIG. 5a is a graphical representation of intensity ratios for red and orange QD types for each of the QD optical codes of FIG. 4a;

FIG. 5b is a graphical representation of usable QD optical codes as a function of minimum ratio intensity difference;

FIG. 7a depicts chemical structures of the main molecules in four commonly used biological buffers, namely, phosphate buffer solution (or "PBS"), carbonate, tris, and HEPES;

FIG. 7b is a graphical representation of varying fluorescence intensities of green, yellow, and orange QD types in each of the buffers of FIG. 7a.

DETAILED DESCRIPTION OF THE PREFERRED EMBODIMENTS

Referring now to FIGS. 1 through 8, there is shown a system and method for deconvolving multiplexed (or "mixed") fluorescence spectral signals generated by quantum dot (or "QD") optical coding technology according to a preferred embodiment of the present invention.

Figure 1:
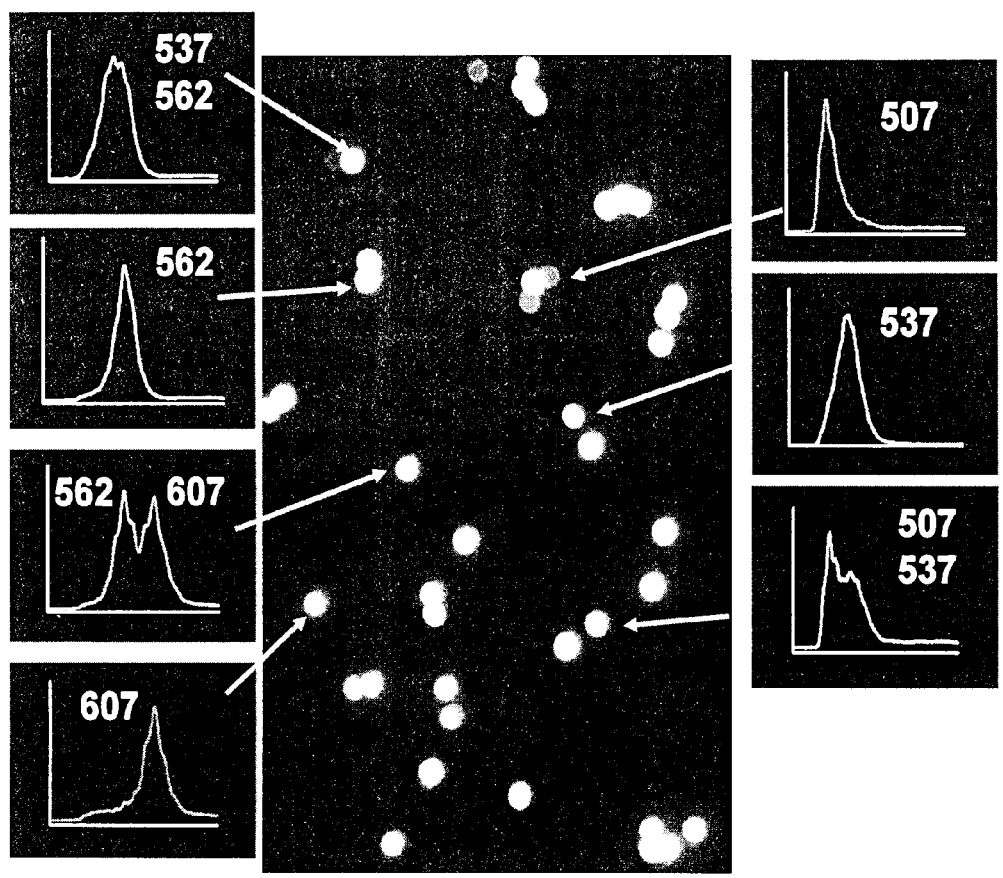
FIG. 1 shows seven different QD optical codes and their corresponding fluorescence spectra, as emitted following excitation with 488 nm radiation.

FIG. 1 shows fluorescence from at least seven different QD optical codes, and respective graphical representations of their corresponding mixed fluorescence spectral signals, following a single excitation (alternately referred to as an "irradiation") with electromagnetic frequency (EMF) radiation having an EMF wavelength of about 488 mm. Each of the QD optical codes may be emitted by one or more QD types present inside a microbead. Preferably, by varying concentrations and emissions of the QD types inside the microbeads, QD optical codes in the form of emitted unique mixed fluorescence spectral signals (alternately referred to as "spectral signatures") may be created, and an optimal set of such QD optical codes may preferably be selected.

Figure 2:
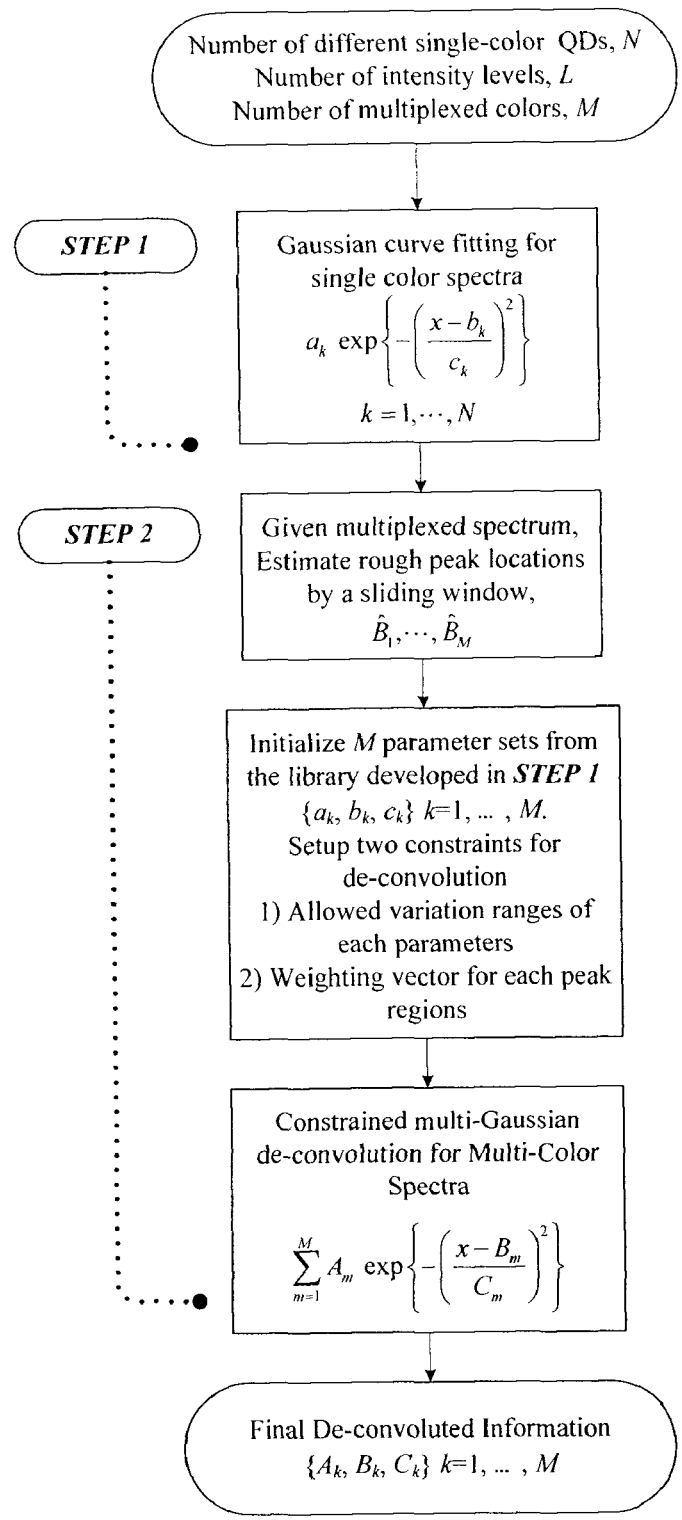
FIG. 2 depicts a two-step deconvolution method according to a preferred embodiment of the present invention.

According to the present invention, and as depicted diagrammatically in FIG. 2, a method of deconvolving multiplexed fluorescence spectral signals of QD optical codes is disclosed. This method may preferably include at least two steps: a curve modeling step and an analysis step (respectively marked as "STEP 1" and "STEP 2" in FIG. 2).

Initially, in the curve modeling step, component single-color fluorescence spectra (alternately referred to as a "fluorescent emission spectrum") for each of the QD types (alternately referred to as "single-color QDs") which are contemplated for use in the QD optical codes are preferably measured by a fluorometer. Preferably, Gaussian curve modeling of the measured data for each of the component single-color fluorescence spectra may be carried out using a so-called Trust-Region (TR) fitting method. [See, for example: J. J. More, D. C. Sorensen, SIAM J. Sci. and Stat. Comp. 1983, 4, 553; and M. A. Branch, T. F. Coleman, Y. Li, SIAM Comp. 1999, 21, 1.1] The TR fitting method may preferably utilize a non-linear optimization algorithm adapted to minimize the first two terms of the Taylor approximation to an error function (i.e., a difference between data and objective curve function). According to this aspect of the invention, and as shown in FIG. 2, the fluorescent emission spectrum for each of the single-color QDs may preferably be represented by three parametric values—namely, a, b, and c. Accordingly, each single-color fluorescent emission spectrum may be represented by one such Gaussian parameter set. Moreover, a spectral database (alternately referred to as a "spectral reference library") of the Gaussian parameter sets for each of the single-color QDs is developed to be used as a reference in later de-convolving the multiplexed fluorescence spectral signals (each, alternately referred to as, a "multiplexed spectrum").

Next, in the analysis step (shown as "STEP 2" in FIG. 2), after the QD optical codes are spectrally read, the multiplexed spectra for the QD optical codes are preferably analyzed in a stepwise-manner. The method is preferably designed so that the read-out of the QD optical codes is relatively rapid, substantially without compromising the accuracy thereof. According to this aspect of the method, an initial identification of the component single-color fluorescence spectra (alternately referred to as "single-color QD spectra") is preferably conducted based on a sliding window method. That is, the number and location of local peaks in the mixed fluorescence spectral signal are preferably first estimated. This initial estimation is referenced as rough peak locations in FIG. 2, since the initial estimation may not provide exact information concerning the local peaks in the multiplexed spectrum. Then, two constraints for deconvolution are preferably imposed on the multi-Gaussian TR-fitting for the multiplexed spectrum. These two imposed constraints are preferably (1) assigned variation ranges of the detected local peak parameter sets {a, b, c}, and (2) imposed weighing factors for the peak region excluding the background region. The constraints may preferably play an important role in evaluating accurate local peak information (e.g., wavelength, emission strength, width), and the constraints may also preferably prevent false identification of, or reduce the chances of falsely identifying, optical codes. Optimizing the parameter sets, the spectral signature is preferably deconvolved into a sum of Gaussians, which is preferably translated into an optical code read-out. In other words, according to the invention, each multiplexed spectrum is preferably de-mixed (or de-multiplexed) into multiple single-color fluorescence spectra, so as to differentiate the fluorescence spectra of different QD types in a mixture or art optical code.

Figure 3:
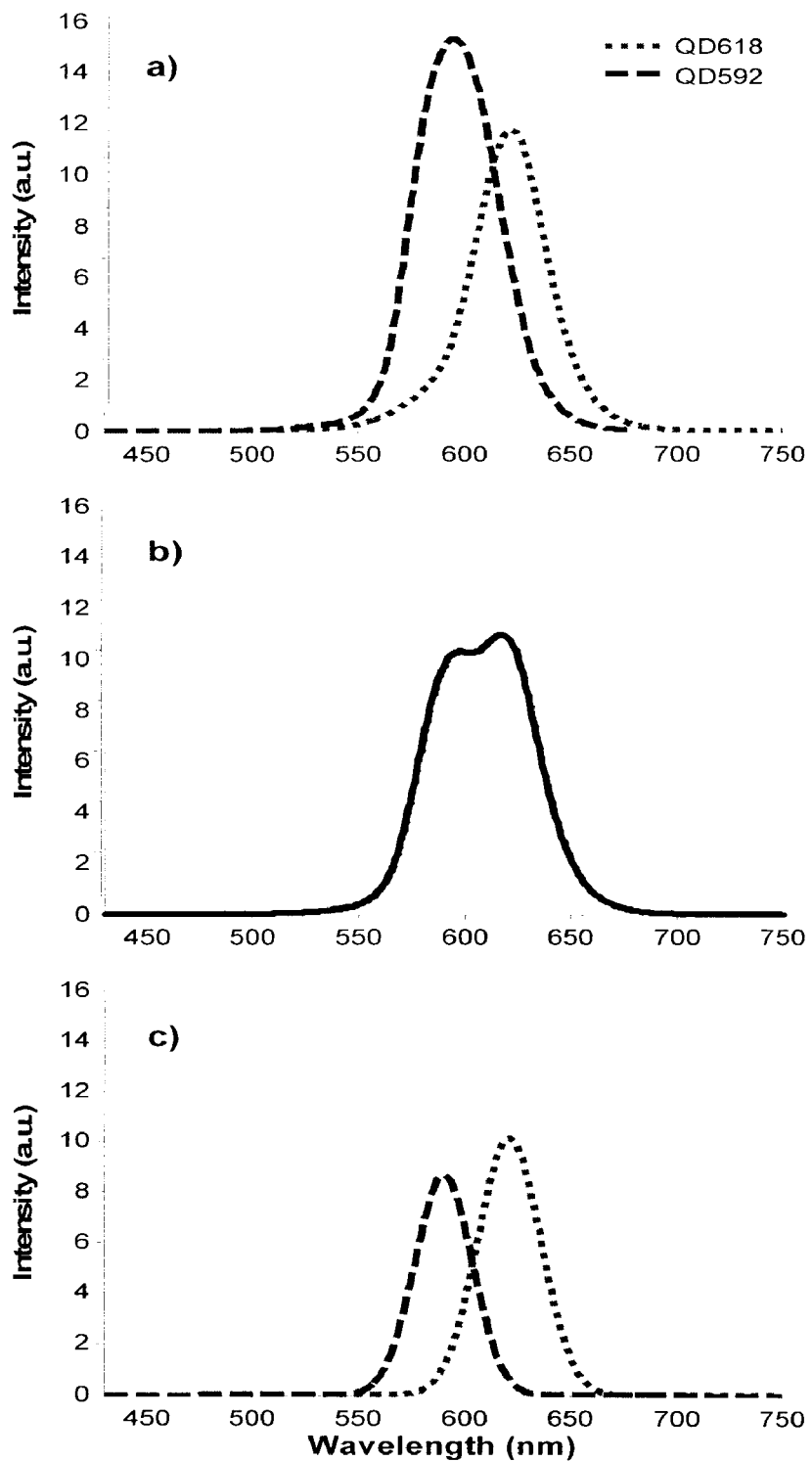
Figure 4:
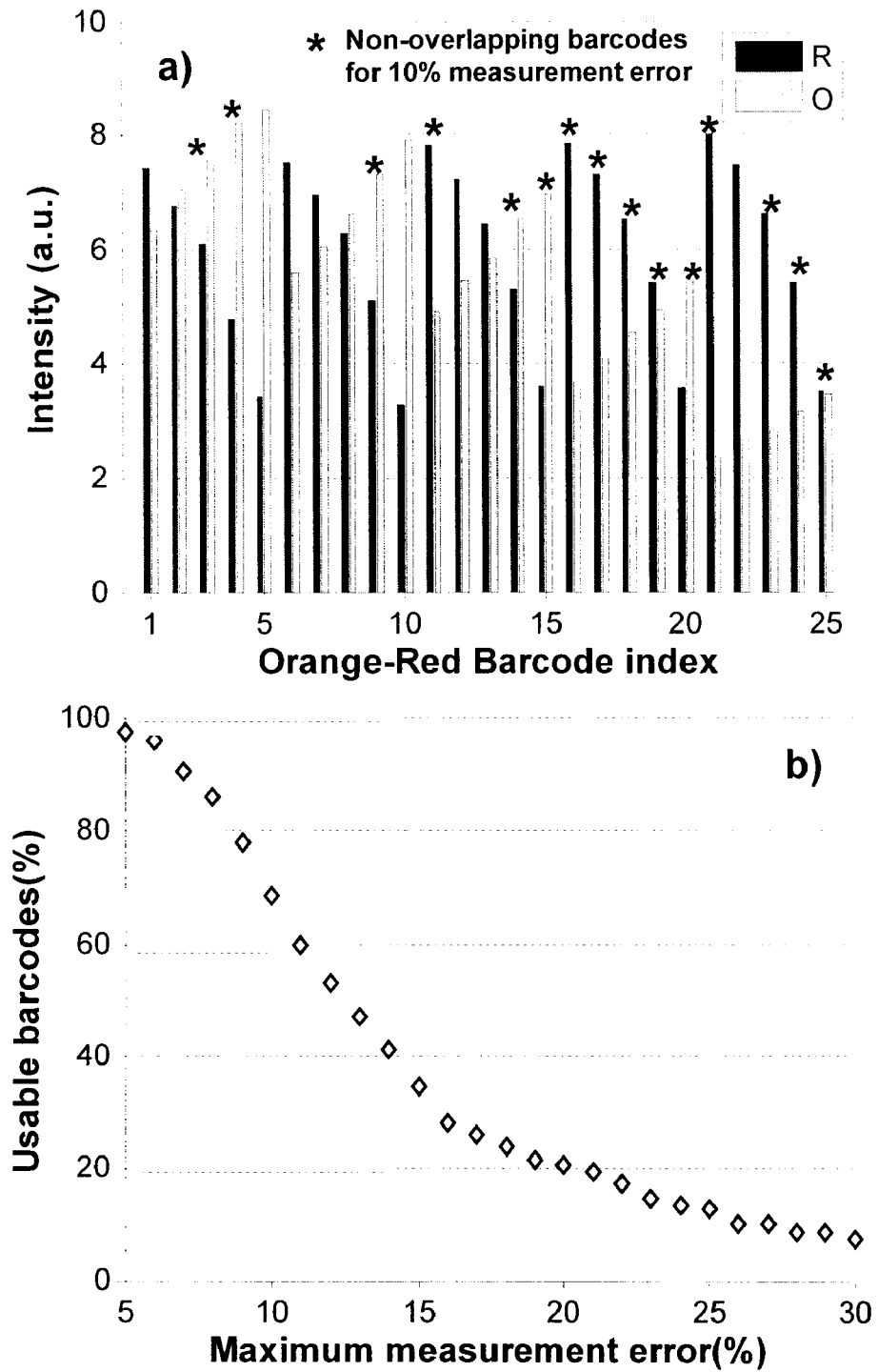
FIG. 4a is a graphical representation of measured intensities for red and orange QD types in twenty-five different QD optical codes.
FIG. 4b is a graphical representation of usable QD optical codes as a function of maximum measurement error.
Figure 5:
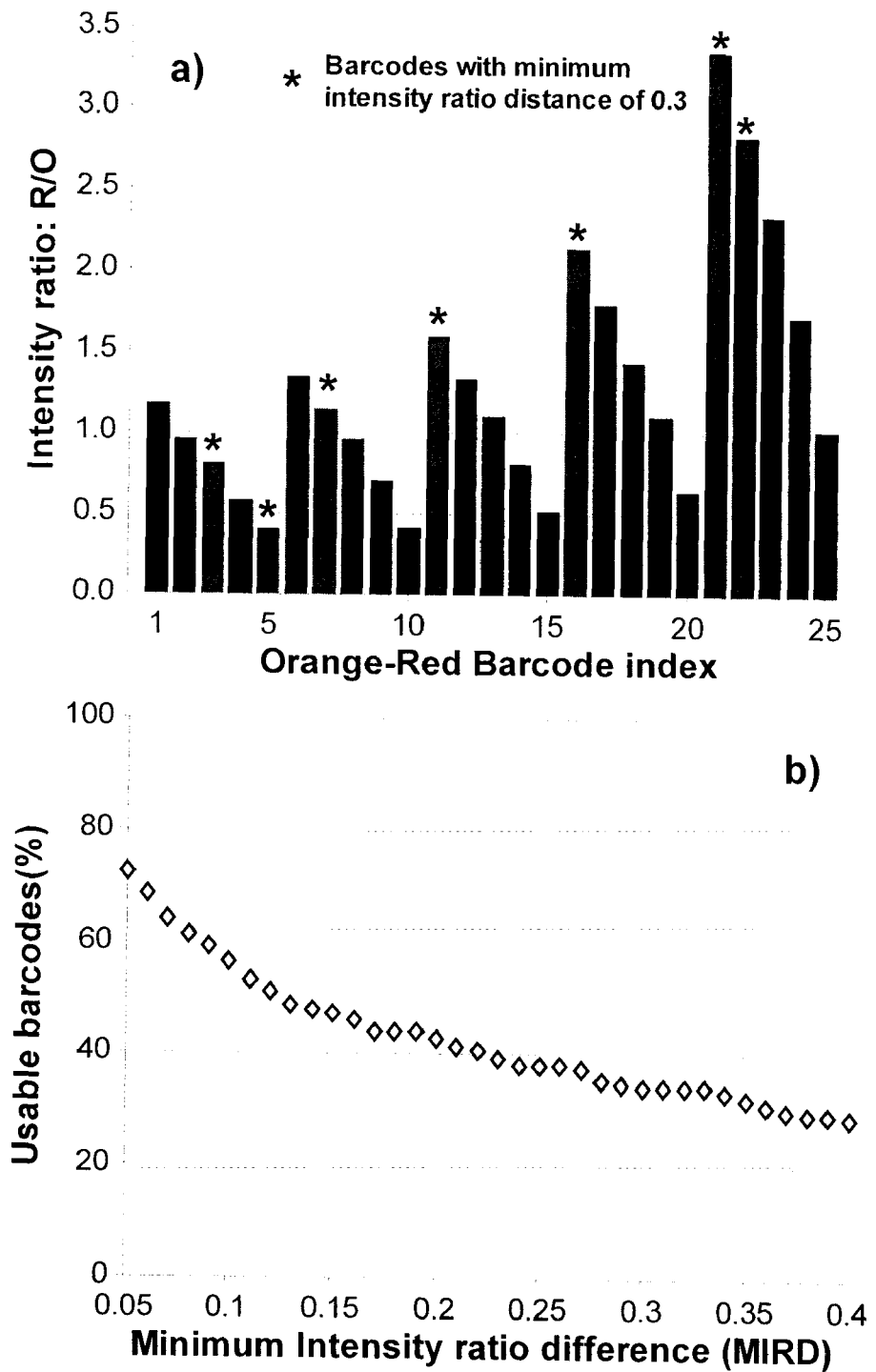
Figure 6:
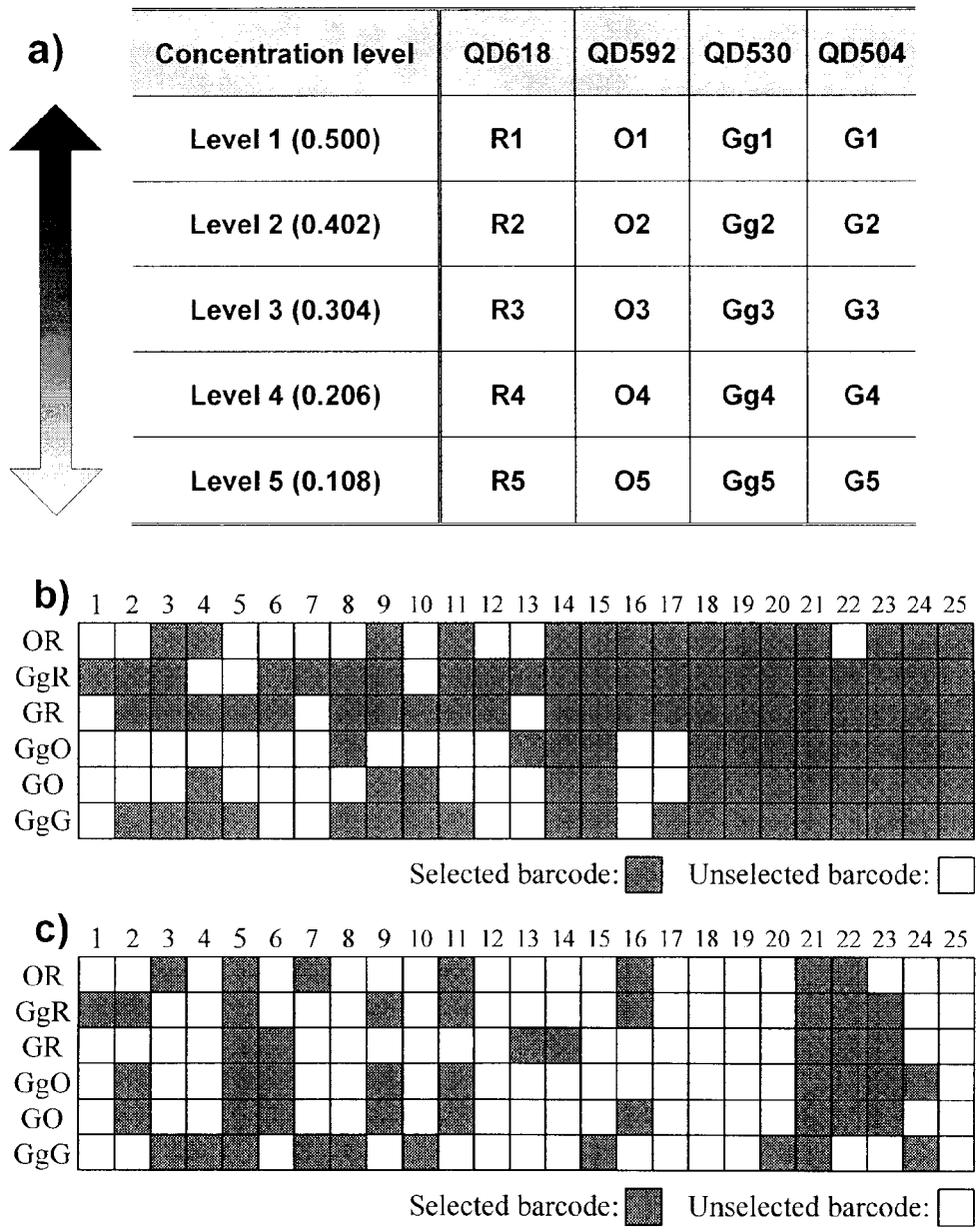
FIG. 6a is a tabulated representation of four different single-color QD types, each provided in five different intensities (or concentrations)
FIG. 6b is a tabulated representation of selected usable QD optical codes differentiable by absolute fluorescence intensities, given a predetermined maximum measurement error in the order of about ten percent.
FIG. 6c is a tabulated representation of selected usable QD optical codes differentiable by ratiometric techniques, given a predetermined minimum ratio intensity difference (MIRD) in the order of about 0.3.

As an example, in FIG. 3, the method of deconvolution is demonstrated using two different QD types—having unique emission profiles at 592 nm and 618 nm—in solution. Initially, the fluorescence spectra of the single-color QD types are preferably measured. These measurements are graphically represented in FIG. 3a. It may be appreciated that the distance between the two peaks shown in FIG. 3a is less than 30 nm. When they are combined in solution, measurement of the multiplexed spectrum may preferably reveal a broad fluorescence peak range between about 550 nm and about 660 nm, as shown in FIG. 3b. After performing the analysis step, according to the invention, the deconvolved fluorescence peaks for the single-color fluorescence spectra (as shown in FIG. 3c) may preferably have a similar appearance to the measured fluorescence spectra emitted by the single-color QD types (shown in FIG. 3a). Upon consideration of FIGS. 3a and 3c, it may be appreciated that the deconvolved fluorescence spectra preferably have similar emission wavelengths to the measured fluorescence spectra, but with different intensities. FIGS. 3a and 3c may preferably help to illustrate the accuracy of the method and system according to the present invention, in deconvolving a multiplexed spectrum into its component single-color spectra, even where the component single-color spectra may have a large degree of spectral overlap. As may be readily appreciated by persons having ordinary shill in the art, the method and system according to the present invention may preferably be generalized (and/or specifically adapted) for optical codes composed of more than two colors.

Thus far, the method and system according to the present invention has been applied to deconvolve one hundred and fifty (150) two-color QD optical codes, spanning five intensity levels and using a spectral database or library of four (4) differently colored QD types (see FIG. 6a).

It may be worthwhile to stress that the ability to deconvolve fluorescence spectra addresses an important challenge for QD optical code (read-out) technologies, namely, that the number of discernable QD optical codes is also dependent upon instrumental measurement error and upon the decoding scheme utilized. Accordingly, it may be important to note that the present invention also extends to encompass two methods and systems for optical code discrimination (preferably, both in conjunction with the systems and methods discussed thus far, and apart from them).

According to the first such method and/or system, the QD optical codes may be selected and/or discriminated based on the intensities of each of the incorporated or component QD types. Upon measuring the fluorescence of substantially uniform mixtures of two (2) different colors of QD types in solution, the individual peak intensities may preferably be identified by the deconvolution methods and systems discussed above. At five concentration levels for each of the two (2) different colors of QD types, there are twenty-five (25) potential QD optical codes for each of the two-color combinations—and the total number of two-color combinations selected from four (4) differently colored QD types, each provided at five different concentration levels, is one hundred and fifty (150). For example, in FIG. 4a, twenty-five (25) deconvolved intensities of Orange-Red combinations are graphically depicted in a sequence of O1R1-5, O2R1-5, O3R1-5, O4R1-5, O5R1-5.

According to the present invention, measurement error is disclosed as affecting the number of available optical codes by overlapping of fluorescence intensities between different optical codes of the same two-color combination group. According to the invention, if an optical code in a two-color combination group may potentially overlap with any other optical code in the same group (given a potential measurement error), then one of the optical codes is preferably screened out due to ambiguity. Using this inventive discrimination method, and given a maximum allowable measurement error of ten percent (10%), the final number of unique and usable optical codes for the Orange-Red combination group is fifteen (15)—i.e., out of the possible twenty-five (25). Each of these usable optical codes is marked with a black asterisk (*) in FIG. 4a.

According to the invention, and as a design guideline, the overall number of usable optical codes may be graphically plotted against the maximum allowable error values (such as shown in FIG. 4b). Clearly, therefore, it may be necessary to carefully balance a desire to minimize potential false readouts against a desire to maximize the number of usable optical codes. In other words, assays requiring a greater number of optical codes may tend to afford diminished measurement error (thereby increasing the demand for instrument measurement precision).

According to the second method and/or system for optical code discrimination, the QD optical codes may be selected and/or discriminated based on the ratio of QD fluorescence intensities for the incorporated or component QD types (alternately referred to as a "ratiometric technique"). According to the invention, this ratiometric technique may be used to differentiate the different optical codes from one another, and/or to select an optimal set of optical codes for use in an assay. FIG. 5a graphically illustrates the potential to discriminate between different optical codes in the same two-color combination group, using the ratiometric technique, according to the invention. In FIG. 5a, ratios for the Orange-Red combination group are graphically represented. In FIG. 5a, each ratio was obtained by dividing the red QD type peak intensity by the orange QD type peak intensity. Using this technique, the error from measurements may preferably become negligible if the intensities of each color in a optical code are similarly scaled and/or affected—e.g., when bead size and/or doping yields cannot be precisely controlled. A minimum intensity ratio difference (MIRD) may preferably be used as a criterion to determine the discernability of each optical code from another. For example, if a desirable MIRD is predetermined to be 0.3, then only seven (7)—i.e., out of the possible twenty-five (25)—could be used in the Orange-Red combination group. Each of these usable optical codes is marked with a black asterisk (*) in FIG. 5a. Alternatively, if the MIRD is reduced to 0.1, then the number of usable QD optical codes increases to fourteen (14). Conversely, higher MIRDs may preferably reduce the number of usable QD optical codes. According to the invention, by changing the MIRD criterion, it may preferably be possible to alter the reliability of QD optical code identification.

According to the invention, and as a design guideline, the overall number of usable optical codes may be graphically plotted against MIRD values (such as shown in FIG. 5b). Use of the ratiometric technique, according to the invention, may preferably enable compensation for potential measurement error through rigorous design of read-out and detection scheme. Generally, selecting an appropriate detection scheme that compensates for known sources and/or patterns of variation in optical code signals may preferably tend to afford increased read-out reliability.

By applying the described discrimination methods to the one hundred and fifty (150) possible two-color optical codes produced from the twenty (20) QD samples indicated by FIG. 6a, it is possible to determine (according to the invention) a practical number of available optical codes for use in high-throughput multiplex detection applications. Using the absolute intensity criterion, and assuming a measurement error of ten percent (10%), then only about sixty-nine percent (69%)—i.e., 103 out of 150—of the entire optical code set is usable (as tabulated in FIG. 6b). On the other hand, using the ratiometric technique, and an MIRD value of 0.3, then only about thirty-four percent (34%)—i.e., 51 out of 150—of the entire optical code set is usable (as tabulated in FIG. 6c). Of course, persons having ordinary skill in the art may appreciate that this analysis might be readily generalized (and/or specifically adapted for application) to a greater number of optical codes built from more extensive libraries. In so doing, such a person might preferably determine the maximum number of practical QD optical codes available for use in a particular assay.

Figure 7:
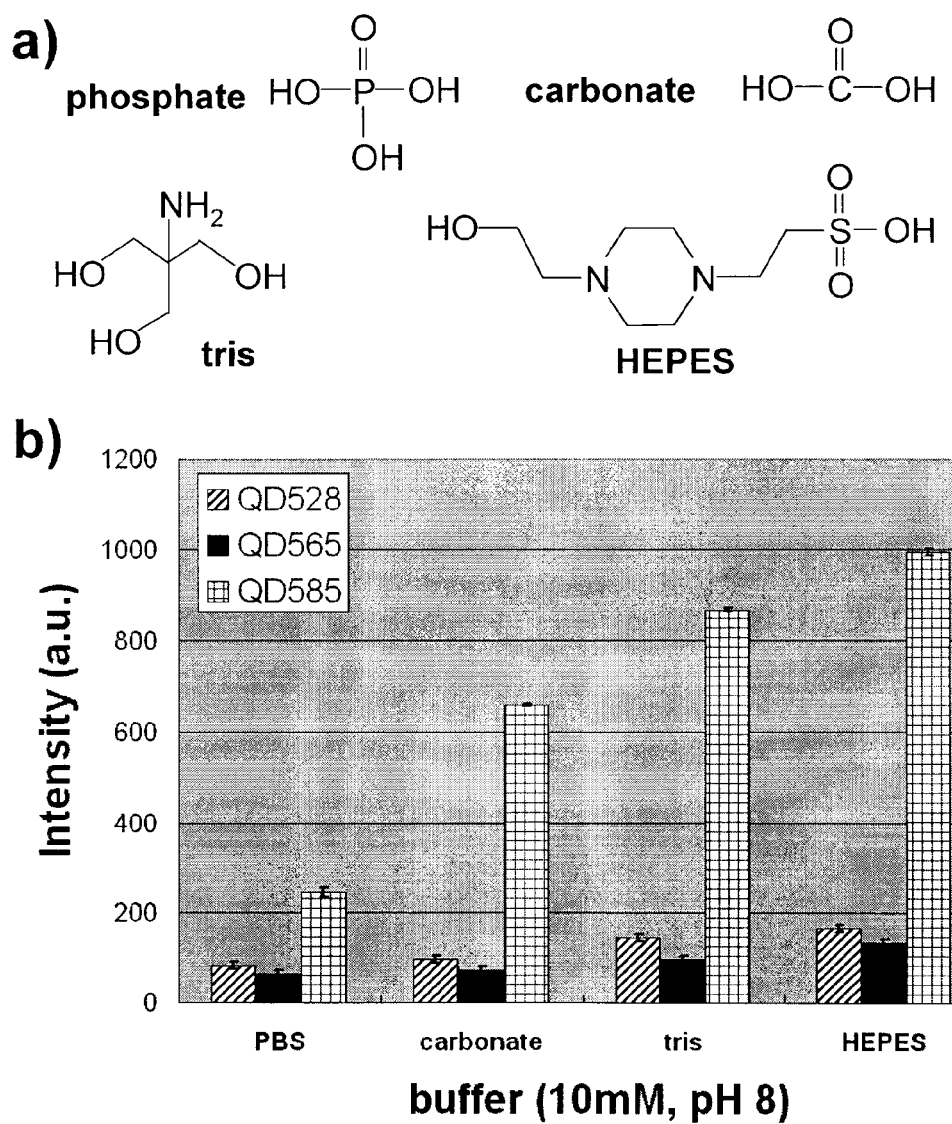

In addition to the detection scheme utilized, environmental factors may also impact upon the accuracy of QD optical code discrimination and identification. FIG. 7b provides a graphical representation of the effect of certain buffer types—PBS, carbonate, tris, and HEPES—(at a given pH) on the fluorescence of three (3) differently colored QD types inside microbeads. According to the invention, it may preferably be appreciated that the buffer used for storage, and for conducting assays, influences the multiplexed signals of the QD optical codes. According to the invention, three differently colored QD types were shown to change fluorescence intensity in the four different buffers. In view of FIG. 7, it may be appreciated that the intensity is lowest in PBS, followed in sequence by carbonate, his, and HEPES buffers. It should also be appreciated, however, that FIG. 7 illustrates a large difference in the magnitude of variation between the different studied QD types. Fluorescence may be seen to vary by 122±32.2% for a green QD type that exhibits a spectral peak at around 528 nm (alternately referred to as "QD528"), to vary by 91±43.1% for a yellow QD type that exhibits a spectral peak at around 565 nm (alternately referred to as "QD565"), and to vary by 691±47.5% for an orange QD type that exhibits a spectral peak at around 585 nm (alternately referred to as "QD585").

In FIG. 7b, and as aforesaid, the green, yellow, and orange QD types emit single-color fluorescence spectra approximately centered around 528 nm, 565 nm, and 585 nm. The four biological buffers tested in FIG. 7b were provided at substantially the same concentration (10 mM) and at a pH of 8. It may be appreciated from FIG. 7b that, for all of these QD types, the fluorescence in PBS is generally substantially less than the fluorescence in carbonate, which is generally substantially less than the fluorescence in tris, and which in turn is generally substantially less than the fluorescence in HEPES. Perhaps notably, QD585 shows the greatest degree of variation in fluorescence among the four buffers. Error bars in FIG. 7b may preferably indicate the 95% confidence interval on mean normalized fluorescence.

As can be seen in FIG. 7b, QD585 has a much larger variation range over QD528 and QD565. This variation range has also been observed by Boldt et al. [see, for example, K. Boldt, *J. of Phy. Chem. B*, 2006, 110, 1959], who may have generally found that larger quantum dots are less stable towards their chemical environment than smaller ones. The surface area of a CdSe core for QD585 may be generally thought to be in the order of about 141% greater than the surface area of a CdSe core for QD528, and about 55% greater than that for QD565. Though not essential to the working of the present invention, it may be generally thought that this greater surface area may allow for more interaction between the QD and the environment, thereby increasing the effect of the QD's chemical environment on the intensity of its fluorescence.

Figure 8:
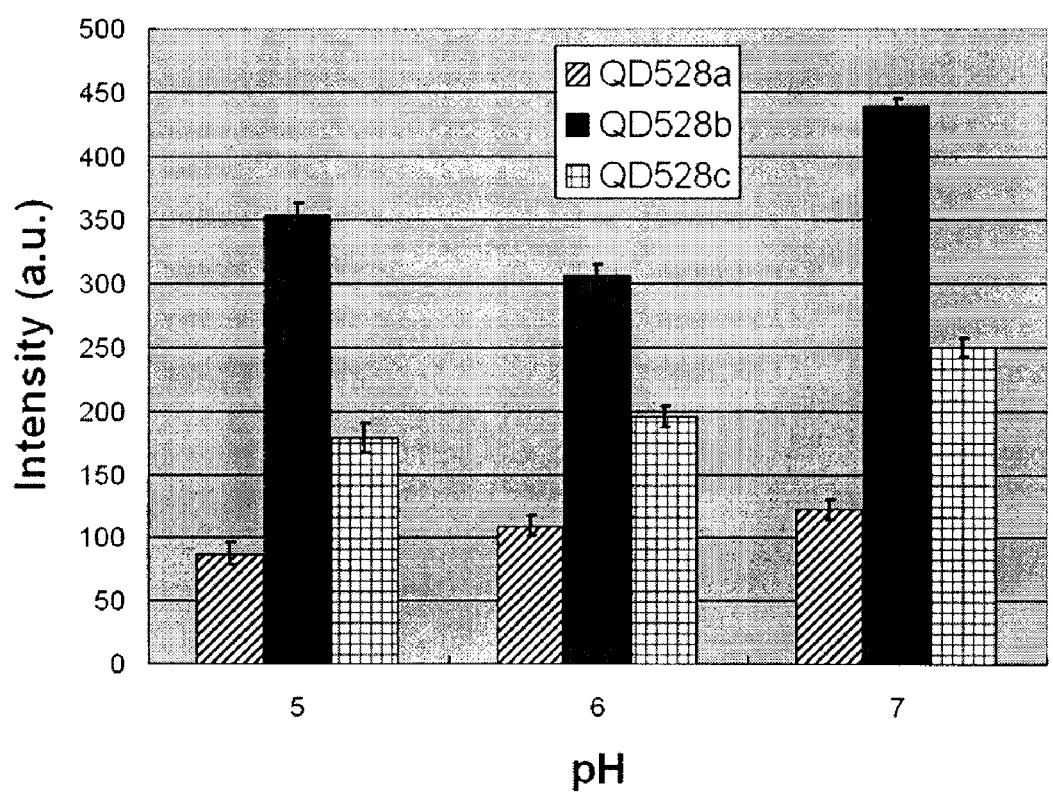
FIG. 8 is a graphical representation of variations in fluorescence intensity of a green QD (QD528) with different amounts of ZnS capping in a citric acid buffer, having a pH of 5~7.

FIG. 8 provides a graphical representation of fluorescence intensities for QD528 with different amounts of ZnS capping in a citrate buffer with pH 5, pH 6, and pH 7. This range of pHs is significant because it may preferably be used in many biological assays. In FIG. 8, QD528a may preferably have a smaller amount of ZnS capping than QD528b, which may, in turn, preferably have a smaller amounts of ZnS capping than QD528c.

Generally, and as may be appreciated from a consideration of FIG. 8, QD528 may show a higher fluorescence in higher pH buffers. The fluorescence of each of the QDs may preferably be generally found to increase with increasing pH. In FIG. 8, the amount of fluorescence variation differs amongst different QDs. Error bars indicate the 95% confidence interval on mean normalized fluorescence.

This trend of increasing fluorescence of QDs with increasing pH may preferably also be seen with other buffers including tris, HEPES, PBS and borate. In 10 mM citric acid (such as may preferably have been used in collecting the data graphically represented in FIG. 8), these green QDs showed between 40%-43% change in fluorescence between pH 5~7. Yellow and orange QDs with different amounts of ZnS capping may vary in fluorescence between 22%-345% in a citrate buffer having a pH of 5~7. Such a large variation may serve to emphasize the importance of, and/or preference for, studying these variations before QD types are used in quantitative applications, since what may be observed for one sample of QDs may not necessarily be repeated in another sample. In all the studies described above, UV-vis spectroscopy did not show any QDs in the supernatant, preferably indicating that the variation in fluorescence intensity was not due to leakage of QDs from the microbeads.

It may be lastly noted that fluorescence signals may also be affected by at least two other processes: (1) leakage of QDs out of the microbeads, such as may be driven, for example, by a diffusion process; and/or (2) photobrightening of QDs, such as may result, for example, from photo-oxidation and/or capping-ligand interactions.

In view of all of the foregoing, and because of potential fluctuations in QD signals emanating from inside microbeads, it may be generally believed that the use of absolute intensity as an optical code discrimination method may be less successful in reliably identifying QD optical codes (i.e., in comparison to the ratiometric technique). It may be additionally believed that, even though the ratiometric technique may lead to a decreased availability of usable optical codes (i.e., in comparison to the absolute intensity method), the ratiometric technique may be somewhat more successful in reliably identifying QD optical codes. The ratiometric intensity may provide a more robust criterion, since it takes into account a number of factors that may cause variation. For example, in FIG. 7b, the absolute intensities of green (QD528), yellow (QD565), orange (QD585) QDs show substantial variations of about 32.2%, 43.1%, and 47.5%, respectively, in different buffers. Using a ratiometric intensity of yellow/green, however, it may preferably be possible (according to the invention) to reduce the variation to as low as about 8.5%. As such, the ratiometric technique may work more reliably than the absolute intensity method.

In conclusion, it is worthwhile to once again note that the read-out or detection scheme and environmental factors may determine the number of usable QD optical codes in biological assays. Despite the proposed feasibility to synthesize in excess of one million optical codes from a library of six (6) differently colored QD types, each available in ten (10) intensity levels, the present invention discloses that practical limitations may exist from the perspective of the read-out and/or detection schemes utilized. According to the invention, and based on the method of discrimination, the practically discernable number of optical codes may preferably be determined.

The method and system provided according to the present invention may preferably be used to deconvolve a multiplexed spectrum into the fluorescence spectra of multiple single-color QD types.

The method and system provided according to the present invention may also preferably be independently used to differentiate one QD signal (and/or one optical code) from another when multiple-emitting QD types are mixed in solution.

The parameters imposed by the decoding system may also preferably be used to direct the design and/or selection of QD optical codes for high accuracy and/or rapid read-out and detection.

Furthermore, the present invention takes the first steps towards identifying more complex systems and methods that may be required, in the future, on account of potential variabilities in fluorescence emission for QDs in the biological environment (which may also place its own limitations on the number of usable optical codes). While a number of challenges may stand ahead, many have been faced and overcome according to the present invention, so as to make better applications of existing QD optical coding technology for use in biological and medical applications—applications that could not have been achieved using prior detection systems and methods.

Experimental Protocols

Synthesis of ZnS-capped CdSe Nanocrystals. ZnS-capped, CdSe QDs were synthesized using a previously described organometallic procedure. [See, for example, C. B. Murray, D. J. Norris, M. G. Bawendi, *J. Am. Chem. Soc.,* 1993, 115, 8706; and M. A. Hines, P. Guyot-Sionnest, *J. Phys. Chem.,* 1996, 100, 468.] The green (504, 528, 530 nm emissions), yellow (565 nm emission), orange (585, 592 nm emissions) and red (618 nm emission) CdSe QD cores were made in three separate reactions. The green, yellow, orange, and red description refers to the fluorescence color emission of the QDs. In each reaction, once the core was made, the vessel was cooled to 270° C. and the capping solution (consisting of diethylzinc and hexamethyldisilathiane in tri-n-octylphosphine) was added to produce the ZnS capping layer on the CdSe core.

FIG. 1. QD-barcodes are prepared by using a two-step method: (1) polystyrene microbeads are either synthesized in-house or purchased and (2) tri-n-octylphosphine oxide coated ZnS-capped CdSe QDs [see, for example: C. B. Murray, D. J. Norris, M. G. Bawendi, *J. Am. Chem. Soc.,* 1993, 115, 8706; M. A. Hines, P. Guyot-Sionnest, *J. Phys. Chem.,* 1996, 100, 468; B. O. Dabbousi, J. Rodriguez-Viejo, F. V. Mikulec, J. R. Heine, H. Mattoussi, R. Ober, K. F. Jensen, M. G. Bawendi, *J. Phys. Chem. B,* 1997, 101, 9463; and X. Peng, M. C. Schlamp, A. V. Kadavanich, A. P. Alivisatos, *J. Am. Chem. Soc.,* 1997, 119, 7019] is mixed with polystyrene microbeads. The QDs enter the microbeads via diffusion and are maintained inside the microbeads by hydrophobic-hydrophobic interactions. Further, they can be sealed inside the microbeads chemically using a silane reaction. There are other methods to prepare QD-barcodes. The Nie method was used because it is a simplest way to prepare the barcodes and it provides barcodes with the highest microbead size uniformity. Spectra were taken of microbeads flowing in a polydimethylsiloxane (PDMS) microfluidic channel (100 μm wide by 15 μm high) using electrokinetics. QDs in the beads were excited using a 488 nm Ar laser (COHERENT, Santa Clara, Calif.) line at 25 mW, focused to an 8 μm spot size using a 60× oil immersion objective (1.35 NA, Olympus, Center Valley, Pa.). Fluorescence was collected using the same objective, dispersed using a grating (Acton Research Corp., Acton, Mass.) and the spectrum measured using a thermo-electrically cooled CCD array camera (Princeton Instruments Inc., Trenton, N.J.). Integration time of the camera was set to 50 msec. Background signals were subtracted.

FIG. 3-6. Concentrations of the constituents of four color groups were controlled based on the absorption at the quantum-confinement peak wavelength, which is the lowest excited energy state. [See, for example, W. C. W. Chan, et. al, *Curr. Opin. in Biotech.* 2002, 73, 40-46.] The four initial most concentrated single-color QD solution samples (named R1, Y1, Gg1, and G1 in the 'Level 1' row), were prepared to have equal 0.50 absorbance. The other less concentrated samples were sequentially diluted in chloroform with absorption step size of 0.098 and the final least concentrated sample has 0.108 absorption. The two color multiplexing out of the four colors (corresponding to N=4, L=5, M=2 in FIG. 2) yields 6 different two-color combinations, i.e., RY, RGg, RG, YGg, YG, GgG, and each of 25 combinations producing distinct QD barcodes were prepared by mixing them together at a 1:1 ratio. All spectra were measured by Fluoromax-3

FIGS. 7 and 8. QDs, dissolved in chloroform were mixed in propanol at a 15% V/V ratio to make a solution with a final QD concentration of at least 3 μm. 5 μm polystyrene microbeads from Bang's Laboratories were added and the solution was shaken overnight. The microbeads were mixed with an excess of 108 QDs per bead. QDs enter the pores of the polystyrene microbeads and remain embedded in the polystyrene through hydrophobic-hydrophobic interactions. The QD-stained microbeads were then washed three times in propanol, dried and re-suspended in aqueous buffers of various concentrations and pH. They were incubated overnight at room temperature and then the fluorescence intensity was measured through flow cytometry. A Coulter Epics XL flow cytometer was used to measure the fluorescence of the QD-stained beads in various buffers. The flow cytometer measured the fluorescence emission, side scatter and forward scatter of 10,000 particles in each sample. As some of these particles may be aggregates of microbeads, broken microbeads, or aggregates of quantum dots, forward scatter and side scatter, which can be correlated to the size and granularity of particles were used to single out the population of monodisperse microbeads from larger aggregates and smaller particles. Only the fluorescence of these single microbeads was used in further analysis to calculate the mean and confidence interval for the fluorescence of each type of QD in the different buffers. To make QDs with the same core but different amounts of the capping solution, aliquots were taken after the addition of 1.0 ml, 2.0 ml, 3.0 ml of capping solution (0.232 M diethyl zinc, and 0.162 M hexamethyl disilathiante), corresponding to QD528a, QD528b, QD528c, respectively in FIG. 8.

Conclusion

While the above method has been presented in the context of two component fluorescence signals, the method and system are equally applicable to multiplexed fluorescence spectra for optical codes composed of more than two differently colored QD types (and thus more than two component signals).

This concludes the description of a presently preferred embodiment of the invention. The foregoing description has been presented for the purpose of illustration and is not intended to be exhaustive or to limit the invention to the precise forms disclosed. Rather, other modifications, variations and alterations may be used in the design and manufacture of other embodiments according to the present invention (and may be apparent to those skilled in the art in view of the above teachings and disclosures) without departing from the spirit and scope of the invention, which is limited only by the accompanying claims of this application.

What is claimed is:

1. A method of deconvolving a mixed fluorescence spectral signal into its component single-color fluorescence spectra emitted by contributing fluorophore types, wherein the method comprises:
   a) a database providing step of providing a spectral database that contains parameter sets, one for each of the component single-color fluorescence spectra;
   b) a receiving step of receiving one or more encoded optical codes, each in the form of one said mixed fluorescence spectral signal emitted by a combination of the contributing fluorophore types; and
   c) an analysis step, of analyzing each said mixed fluorescence spectral signal, comprising:
      i) a peak estimation substep of using a sliding window technique, with reference to the parameter sets contained in the spectral database, to initially identify and estimate the number and location of local peak regions for each of the component single-color fluorescence spectra;
      ii) a constraint setup substep of assigning allowable variation ranges for each of the parameter sets corresponding to one of the local peak regions for each said component single-color fluorescence spectra; and
      iii) a deconvolution substep of deconvolving the mixed fluorescence spectral signal into a sum of parametric values, with reference to the parameter sets contained in the spectral database, so as to generate a list of its said component single-color fluorescence spectra; whereby each encoded and received one of said optical codes, in the form of one said mixed fluorescence spectral signal, is decoded and identified by its said component single-color fluorescence spectra corresponding to its said contributing fluorophore types.

2. A method according to claim 1, wherein one or more of the contributing fluoxophore types are contributing quantum dot (QD) types, and wherein one or more of the encoded optical codes are encoded QD optical codes.

3. A method according to claim 1, wherein in the constraint setup substep, one or more weighting factors are assigned for each of the local peak regions.

4. A method according to claim 1, further comprising a curve modelling step, before the database providing step, of (i) using an automated non-linear optimization technique to reduce each of the component single-color fluorescence spectra to a Gaussian curve, and (ii) generating and recording, in the spectral database, the parameter sets for each of the component single-color fluorescence spectra; and wherein in the deconvolution substep, the parametric values are Gaussian parametric values.

5. A method according to claim 4, wherein the automated non-linear optimization technique is a trust-region (TR) fitting technique.

6. A method according to claim 4, wherein in the curve modelling step, the automated non-linear optimization technique minimizes the first two terms of a Taylor approximation to an error function.

7. A method according to claim 6, wherein the error function is the difference between data and the objective curve function.

8. A method according to claim 4, wherein in the curve modelling step, the automated non-linear optimization technique is performed according to the formula $$a_k \exp\left\{-\left(\frac{x-b_k}{c_k}\right)^2\right\}$$

$$k = 1, \ldots, N$$

where a, b, and c are three parametric curve values representing each of the component single-color fluorescence spectra, and where N is a number of fluorophore types from which the contributing fluorophore types present in the mixed fluorescence spectral signal are selected; wherein in the database providing step, each of the parameter sets contained in the spectral database is provided in the form {a, b, and c}; wherein in the deconvolution substep, the mixed fluorescence spectral signal are deconvolved according to the formula $$\sum_{m=1}^{M} A_m \exp\left\{-\left(\frac{x-B_m}{C_m}\right)^2\right\},$$

where M is the number of component single-color fluorescence spectra in the mixed fluorescence spectral signal; and wherein the list of the component single-color fluorescence spectra in the mixed fluorescence spectral signal is provided in the form $\{A_k, B_k, C_k\}$ where k=1, ..., M.

9. A method according to claim 1, wherein the contributing fluorophore types in each said combination have measurable absolute fluorescence intensities; and wherein the method further comprises a set selection step, before the receiving step, of selecting an optimal set of the optical codes, with each of the optical codes being selected such that, given a predetermined maximum potential measurement error, measured absolute fluorescence intensities for each said combination of said contributing fluorophore types are discrete from one another.

10. A method according to claim 9, wherein the predetermined maximum potential measurement error is about ten (10) percent.

11. A method according to claim 1, further comprising a differentiation step, after the deconvolution substep, of differentiating the optical codes from one another on the basis of measured absolute fluorescence intensities of the fluorophore types in each said combination, given a predetermined maximum potential measurement error.

12. A method according to claim 1, wherein the fluorophore types in each said combination have calculable fluorescence intensity ratios; and wherein the method further comprises a set selection step, before the receiving step, of selecting an optimal set of the optical codes, with each of the optical codes being selected such that the fluorescence intensity ratios for each said combination are separated from each other by a predetermined minimum intensify ratio difference (MIRD).

13. A method according to claim 12, wherein the predetermined MIRD is about 0.3.

14. A method according to claim 1, further comprising a differentiation step, after the deconvolution substep, of calculating fluorescence intensity ratios of the fluorophore types in each said combination, and differentiating the optical codes from one another by the calculated fluorescence intensity ratios, given a predetermined minimum intensity ratio difference (MIRD) separating the fluorescence intensity ratios of the fluorophore types for each said combination.

15. A method according to claim 1, wherein for each of the optical codes, the combination of the contributing fluorophore types is contained within or secured to a microbead adapted for detection of a target molecule within a clinical sample.

16. A method according to claim 1, further comprising an irradiation step, before the receiving step, of irradiating the combination of the contributing fluorophore types with electromagnetic frequency (EMF) radiation, such that the combination emits the mixed fluorescence spectral signal.

17. A method according to claim 16, wherein in the irradiation step, a laser irradiates the combination.

18. A method according to claim 16, wherein the EMF radiation has an EMF wavelength of about 488 nm.

19. A method according to claim 1, wherein the database providing step, the receiving step, and the analysis step are performed onboard a handheld detection device.

20. A method according to claim 1, wherein the contributing fluorophore types vary from one another based on the color and/or the intensity thereof.

21. A method according to claim 1, wherein each said combination of contributing fluorophore types varies from each other said combination based on the color and/or the intensity of the contributing fluorophore types of each said combination.

22. A method according to claim 1, wherein four colors of contributing fluorophore types are provided, and five intensities for each of said colors of contributing fluorophore types are provided.

23. A system for deconvolving a mixed fluorescence spectral signal into its component single-color fluorescence spectra emitted by contributing fluorophore types, with the system being for use with one or more encoded optical codes, with each of the optical codes being in the form of one said mixed fluorescence spectral signal emitted by a combination of the contributing fluorophore types, wherein the system comprises:

a) a spectral database containing parameter sets, one for each of the component single-color fluorescence spectra;

b) a detection element operatively receiving the optical codes; and c) a signal processor operative to analyze each said mixed fluorescence spectral signal, with the signal processor being encoded (i) to operatively execute a sliding window technique, with reference to the parameter sets contained in the spectral database, for initial identification and estimation of the number and location of local peak regions for each of the component single-color fluorescence spectra; (ii) to assign allowable variation ranges for each of the parameter sets corresponding to one of the local peak regions for each said component single-color fluorescence spectra; and (iii) to operatively deconvolve the mixed fluorescence spectral signal into a sum of parametric values, with reference to the parameter sets contained in the spectral database, so as to generate a list of its said component single-color fluorescence spectra; whereby the system decodes and identifies each encoded and received one of said optical codes, in the form of one said mixed fluorescence spectral signal, by its said component single-color fluorescence spectra corresponding to its said contributing fluorophore types.

24. A system according to claim 23 adapted for use with contributing quantum dot (QD) types as one of more of the contributing fluorophore types, and encoded QD optical codes as one or more of the encoded optical codes.

25. A system according to claim 23, wherein the signal processor is additionally encoded to assign one or more weighting factors for each of the local peak regions.

26. A system according to claim 23, further comprising a fluorometer to measure the component single-color fluorescence spectra for each of the contributing fluorophore types, and a spectral processor encoded to operatively reduce each of the component single-color fluorescence spectra to a Gaussian curve; and wherein the parametric values comprise Gaussian parametric values.

27. A system according to claim 23, wherein the spectral processor reduces each of the component single-color fluorescence spectra to said Gaussian curve according to the formula $$a_k \exp\left\{-\left(\frac{x-b_k}{c_k}\right)^2\right\}$$
$$k = 1, \ldots, N$$

where a, b, and c are three parametric curve values representing each of the component single-color fluorescence spectra, and where N is a number of fluorophore types from which the contributing fluorophore types present in the mixed fluorescence spectral signal are selected; wherein each of the parameter sets contained in the spectral database is provided in the form {a, b, and c}; wherein the signal processor deconvolves the mixed fluorescence spectral signal according to the formula $$\sum_{m=1}^{M} A_m \exp\left\{-\left(\frac{x-B_m}{C_m}\right)^2\right\},$$

where M is the number of component single-color fluorescence spectra in the mixed fluorescence spectral signal; and wherein the list of the component single-color fluorescence spectra in the mixed fluorescence spectral signal is provided in the form ($A_k$, $B_k$, $G_k$ where k=1, ..., M.

28. A system according to claim 23, wherein the detection element is operative to measure absolute fluorescence intensities of contributing fluorophore types in each said combination; and wherein the system further comprises a predetermined set of the optical codes, with each of the optical codes in the predetermined set being such that, given a predetermined maximum potential measurement error, the absolute fluorescence intensities measured for each said combination of said contributing fluorophore types are discrete from one another.

29. A system according to claim 28, wherein the predetermined maximum potential measurement error is about ten (10) percent.

30. A system according to claim 23, wherein the signal processor is additionally encoded to operatively differentiate the optical codes from one another on the basis of measured absolute fluorescence intensities of the fluorophore types in each said combination, given a predetermined maximum potential measurement error.

31. A system according to claim 23, wherein the signal processor is operative to calculate fluorescence intensity ratios of the fluorophore types in each said combination; and wherein the system further comprises a predetermined set of the optical codes, with each of the optical codes in the predetermined set being such that the fluorescence intensity ratios for each said combination are separated from each other by a predetermined minimum intensity ratio difference (MIRD).

32. A system according to claim 31, wherein the predetermined MIRD is about 0.3.

33. A system according to claim 23, wherein the signal processor is additionally encoded (i) to operatively calculate fluorescence intensity ratios of the fluorophore types in each said combination, and (ii) to differentiate the optical codes from, one another by the calculated fluorescence intensity ratios, given a predetermined minimum intensity ratio difference (MIRD) separating the fluorescence intensity ratios of the fluorophore types for each said combination.

34. A system according to claim 23, further comprising a microbead containing or securing the combination of the contributing fluorophore types for each of the optical codes, with each said microbead being adapted for detection of a target molecule within a clinical sample.

35. A system according to claim 23, further comprising an irradiating element to operatively irradiate the combination of the contributing fluorophore types with electromagnetic frequency (EMF) radiation, such that the combination emits the mixed fluorescence spectral signal.

36. A system according to claim 35, wherein the irradiating element is a laser.

37. A system according to claim 35, wherein the EMF radiation has an EMF wavelength of about 488 run.

38. A system according to claim 23, further comprising a handheld detection device enclosure substantially enclosing the detection element and the signal processor, with the spectral database being carried onboard the handheld detection device.

39. A system according to claim 23 adapted for use with fluorophore types that vary from one another based on the color and/or the intensity thereof.

40. A system according to claim 23 adapted for use with four different colors of contributing fluorophore types, and adapted for use with five different intensities for each of said colors of contributing fluorophore types.

* * * * *

UNITED STATES PATENT AND TRADEMARK OFFICE
CERTIFICATE OF CORRECTION

PATENT NO. : 8,360,321 B2  Page 1 of 1
APPLICATION NO. : 12/594430
DATED : January 29, 2013
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 248 days.

Signed and Sealed this
First Day of September, 2015

Michelle K. Lee
*Director of the United States Patent and Trademark Office*